United States Patent [19]

Welborn, Jr.

[11] Patent Number: 5,441,920
[45] Date of Patent: * Aug. 15, 1995

[54] SILICON-BRIDGED TRANSITION METAL COMPOUNDS

[75] Inventor: Howard C. Welborn, Jr., Houston, Tex.

[73] Assignee: Exxon Chemical Patents Inc., Wilmington, Del.

[*] Notice: The portion of the term of this patent subsequent to May 21, 2008 has been disclaimed.

[21] Appl. No.: 161,828

[22] Filed: Dec. 2, 1993

Related U.S. Application Data

[60] Division of Ser. No. 884,450, May 18, 1992, Pat. No. 5,314,973, which is a continuation of Ser. No. 661,274, Feb. 26, 1991, Pat. No. 5,120,867, which is a division of Ser. No. 405,090, Sep. 7, 1989, Pat. No. 5,017,714, which is a continuation of Ser. No. 170,516, Mar. 21, 1989, abandoned.

[51] Int. Cl.$^6$ .......................... C07F 7/02; C08F 4/42; C08F 4/64
[52] U.S. Cl. .................... 502/103; 502/117; 502/152; 526/126; 526/127; 526/160; 526/170; 526/348.2; 526/348.4
[58] Field of Search ................ 502/103, 117, 152

[56] References Cited

U.S. PATENT DOCUMENTS 4,794,096 12/1988 Ewen.

FOREIGN PATENT DOCUMENTS

0129368A1 12/1984 European Pat. Off..

OTHER PUBLICATIONS

Schnutenhaus, et al. "1,1'-Trimethylenebis ($\eta^5$-3-tert-butylcyclopentadienyl)-titanium (IV) Dichloride, a Chiral ansa—Titanocene Derivative", Angew. Chem. Int. Ed. Engl. 18, (1979), pp. 777-778.

Smith, et al., "Molecular Structure and Proton Magnetic Resonance Spectra of Methylene—and Ethylene—Bridged Dicyclopentadienyltitanium Compounds", Journal of Organometallic Chemistry, 173 (1979), pp. 175-185.

Katz, et al., "1-1'-Methylenetitanocene Dichloride", Tetrahedron Letters, No. 28, (1970), p. 2497-2499.

Smith, et al., "ansa-Metallocene Derivatives III. Influence of an Interannular Ethylene Bridge on the Reactivity of Titanocene Derivatives", Journal of Organometallic Chemistry, 218 (1981), pp. 159-167.

Davis, et al., "The Proton and Carbon NMR Spectra of Alkyl Substituted Titanocene and Zirconocene Dichlorides", Journal of Magnetic Resonance, 37, (1980), pp. 441-448.

Klouras, N., "Metallocenophane: $^1$H-NMR-Untersuchungen", Z. Naturforsch, 38b (1983), pp. 321-325.

(List continued on next page.)

*Primary Examiner*—Asok Pal
*Attorney, Agent, or Firm*—M. B. Kurtzman; D. E. Warner

[57] ABSTRACT

Silicon-bridged transition metal compounds and their use as alpha-olefin polymerization catalysts are disclosed. The polymerization catalyst comprises a chiral silicon-bridged metallocene of the following structure:

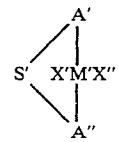

where M is a transition metal, X' and X" are the same or different hydride, halogen, hydrocarbyl or halohydrocarbyl groups having up to about 6 carbon atoms, A' and A" are each the same or different asymmetrical mononuclear or polynuclear hydrocarbyl or silahydrocarbyl moieties and S' is a bridge of 1-4 atoms selected from the group consisting of silanylene, silaalkylene, oxasilanylene, and oxasilaalkylene, and may include an alumoxane. Specifically, the transition metals are titanium, zirconium, and hafnium.

37 Claims, 6 Drawing Sheets

OTHER PUBLICATIONS

Kopf-Maier, et al., "Turmorhemmung durch Metallocene Ring Substituierte und ringüberbrückte Titanocen-dichloride", Eur. J. Med. Chem.—Chimica Therapeutica, No. 16, May-Jun. 1981, pp. 275-281.

Jutzi, et al., "Metallkomplexe mit verbrückten permethylierten Cyclopentadienylligenden", Chemische Berichte, vol. 119, No. 6, (1986), pp. 1750-1754.

Schwemlein, et al., "*ansa*-Metallocene Derivatives via Synthesis of Tetramethylethylene-Bridged Titanocene and Zirconocene Derivatives Via Reductive Fulvene Coupling", Journal of Organometallic Chemistry, 254, (1983) pp. 69-73.

Schwemlein, et al., "*ansa*-Metallocene Derivatives VI. Synthesis and Molecular Structure of a Stable Tetramethylethylene-Bridged Chromocene Carbonyl Complex, $(CH_3)_4C_2(C_5H_4)Cr(CO)$", Journal of Organometallic Chemistry, 256 (1983), pp. 285-289.

Külper, K., "Polymerization Behavior of Soluble Ring-Substituted Zirconocene (IV) Dichlorides and Methyl Alumoxanes as Well as Other Cocatalysts with Respect to 1-Olefins", Dissertation for Ph.D., Jan., 1985.

Langer, A. W., *Lect. Bienn. Polym. Symp.* 7th (1974); *Ann. N.Y. Acad. Sci.* 295, 110-126 (1977).

Ewen, J. A., *J. Amer. Chem. Soc.*, v. 106, p. 6355 (1984).

Boor, Jr. J., *Ziegler-Natta Catalysts and Polymerizations*, Academic Press, New York 1979.

Natta, G., et al., *Chem. Ind. (Milan)* 42, 125 (1960).

Zambelli et al, *Makromol. Chem.* 112, 183 (1968).

Zambelli, et al, *Macromolecules*, v. 16, pp. 341-348 (1983).

Kaminsky, W., et al, *Angew. Chem. Int. Ed. Eng.;* 24, 507-508 (1985).

Natta, *J. Inorg. Nucl. Chem.* 8, 589 (1958).

Wild et al, *J. Organomet. Chem.* 232, 233-47 (1982).

Martin et al, *J. Organomet. Chem.* 97, 261-273 (1975).

Couturier et al, *J. Organomet. Chem.* 195, 291-306 (1980).

Soga et al., *Makromol. Chem. Rapid Commun.* 8, 305-310 (1987).

MIRROR IMAGE RACEMIC FORMS

RACEMIC FORM   ORIENTED MONOMER BINDING

SILICON-BRIDGED TRANSITION METAL COMPOUNDS

This is a divisional application of U.S. Ser. No. 07/884,450 filed May 18, 1992, now U.S. Pat. No. 5,314,973, which is a continuation of U.S. Ser. No. 07/661,274, filed Feb. 26, 1991, now U.S. Pat. No. 5,120,867 which is a divisional of U.S. Ser. No. 07/405,090, filed Aug. 7, 1989, now U.S. Pat. No. 5,017,714 which is a continuation of U.S. Ser. No. 07/170,516, filed 21 Mar. 1989, abandoned.

FIELD OF THE INVENTION

The invention pertains to silicon-bridged metallocene compounds having utility as catalysts for stereoregular α-olefin polymerization.

BACKGROUND OF THE INVENTION

There are four types of tacticity which have been described in poly-α-olefins: atactic, normal isotactic, isotactic stereoblock, and syndiotactic. Although all of these tacticity variations have been primarily demonstrated in the case of polypropylene, they are in theory equally possible for all poly-α-olefins. The random, or atactic structure is represented by a polymer backbone of alternating methylene and methine carbons, with randomly oriented branches substituting the methine carbons. The methine carbons randomly have R and S configurations, creating adjacent pairs either of like configuration (a meso or "m" dyad) or of unlike configuration (a racemic or "r" dyad). The atactic form of a polymer will contain approximately equal fractions of meso and racemic dyads.

In the normal isotactic structure of an α-olefin polymer, all of the monomer units have the same stereochemical configuration, with the exception of random errors which appear in the chain. Random errors will almost always appear as isolated inversions of configuration which are corrected in the very next insertion to restore the original R or S configuration of the propagating chain. These single insertions of inverted configuration give rise to rr triads, which distinguish this isotactic structure in its NMR from the isotactic stereoblock form. Long before anyone had discovered a catalytic system which produced the isotactic stereoblock form of a poly-α-olefin, the possible existence of such a structure had been recognized and mechanisms for its formation had been proposed based on conventional Ziegler-Natta mechanisms in Langer, A. W., *Lect. Bienn. Polym. Symp.* 7th (1974); *Ann. N. Y. Acad. Sci.* 295, 110–126 (1977). The first example of this form of polypropylene and a catalyst which produces it in a pure form were reported in Ewen, J. A., *J. Amer. Chem. Soc.*, v. 106, p. 6355 (1984).

The formation of stereoblock isotactic polymer differs from the formation of the normal isotactic structure in the way that the propagation site reacts to a stereochemical error in the chain. As mentioned above, the normal isotactic chain will return to the original configuration following an error because the stereochemical regulator, the metal and its surrounding ligands, still dictates the same stereochemical preference during insertion. In stereoblock propagation, the site itself changes from one which dictates an R configuration to one which dictates an S configuration. This occurs either because the metal and its ligands change to the opposite stereochemical configuration or because the configuration of the last added monomer, rather than the metal chirality, controls the configuration of the next added monomer. The former case, where the metal changes to the opposite configuration, has been sought but, as far as applicant is aware, has never been observed in a Ziegler polymerization; however, the latter case is now known to be responsible for stereoblock polymerization.

Unlike normal isotactic polymers, the lengths of individual blocks of the same configuration in the stereoblock structure vary widely due to changing reaction conditions. Since only the erroneous parts of the chains affect the crystallinity of the product, in general, normal isotactic polymers and isotactic stereoblock polymers of long block length (greater than 50 isotactic placements) have similar properties.

Syndiotactic polymers have a strong mechanistic similarity to isotactic stereoblock polymers; indeed, the force which results in syndiotactic propagation is the same steric interaction of the last added monomer with the incoming monomer. The most significant difference between the isotactic propagation mechanisms and the syndiotactic propagation mechanism is the mode of addition, which defines which carbon atom of the new monomer becomes bonded to the metal during the insertion step, as reported in Boor, Jr. J., *Ziegler-Natta Catalysts and Polymerizations*, Academic Press, New York 1979. The addition modes of isotactic and syndiotactic propagation are opposite.

Syndiotactic propagation has been studied for over 25 years; however, only a few good syndiospecific catalysts have been discovered, all of which are extremely sensitive to monomer bulkiness. As a result, well-characterized syndiotactic polymers are limited only to polypropylenes. The chain backbone of a syndiotactic polymer can be considered to be a copolymer of olefins with alternating stereochemical configurations. Highly syndiotactic polymers are generally highly crystalline and will frequently have higher melting points than their isotactic polymorphs. However, the frequency of errors in typical syndiotactic polymers (mr triads) is much greater than in the related isotactic stereoblock polymers, possibly due to weaker monomer orientation forces in these catalysts. A frequent error in syndiotactic polypropylenes is an isotactic block of monomers. Mechanisms for the formation of several hypothetical types of stereoregularity, consisting of non-random blocks of the above stereoregular structures, have been proposed in Boor and Langer mentioned above.

Chirality, whether it arises from catalyst crystal structure, surrounding ligand structure, or asymmetry of the growing chain, is essential to polymerize stereoregularly. Polymerization catalysts which lack chirality or have weak or distant asymmetry in their structures will produce either atactic polyolefins or ones of low stereoregularity. The mechanisms by which metallocene catalysts control chain tacticity are based on the same principles as for both conventional and metal-halide catalysts. The identification of two distinct types of catalyst chirality has given rise to two mechanisms for stereochemical induction during polymerization termed the 'site control mechanism' and the 'chain end control mechanism'. For many years there were ongoing arguments about what mechanistic step and what features of the polymerization process played the most important role in stereospecific polymerization. Today, while the arguments have quieted, there is still no single mechanistic interaction which fully explains stereoregular propagation for all of the known stereospecific catalysts, including the metallocenes. Some of the key proposals are reviewed by Boor mentioned above and include: (1) the crystalline asymmetry of the active site, (2) the asymmetry induced by cocatalyst binding, (3) asymmetry introduced by the attached polymer helix, and (4) the asymmetry of the assembled active site. Rather than to select any one effect as most important, the two present-day mechanisms of stereoregulation divide these steric and chiral effects either into catalyst site or chain-end interactions. Even though catalyst site chirality will almost always dominate over chain-end chirality, the chain-end control mechanism in achiral catalysts is responsible for two of the most interesting types of tacticity, stereoblock isotacticity and syndiotacticity.

One of the key features of the chain-end control mechanism for coordinated olefin polymerization is the mode of olefin addition during the propagation step. The two types of olefin addition, primary addition and secondary addition, are shown in the following diagram for polypropylene:

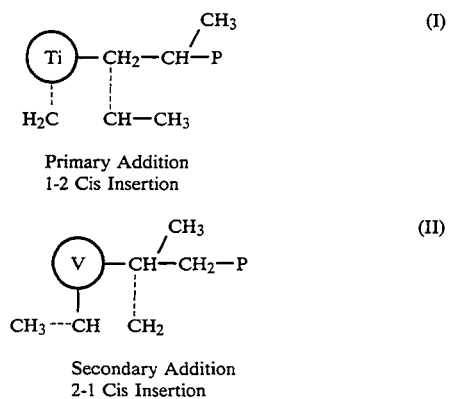

These addition mechanisms are also referred to as '1-2 addition' and '2-1 addition', respectively, indicating the carbon number of the last monomer and the carbon number of the new monomer which will form the new bond. Primary addition is almost exclusively the mode of addition found for titanuim and zirconium catalysts, including metallocene and non-metallocene types and most heterogeneous vanadium catalysts. Secondary addition is common for catalysts in which the alkyl is more 'cationic', such as soluble vanadium catalysts used in low temperature polymerizations. In all cases where the mode of addition has been studied in Ziegler-Natta catalysis, primary insertion has accompanied isotactic polymerization and secondary insertion has accompanied syndiotactic polymerization, although the converse is certainly not true. When visualizing the insertion step using (I) and (II), it is important to remember that olefin insertion in Ziegler-Natta polymerization always takes place in a CIS manner, as shown, meaning that the coordinated face of the olefin always attaches to the existing alkyl-metal bond. Inversion of neither the alkyl carbon configuration nor the olefin-metal carbon configurations occurs, as originally reported by Natta, G., et al, *Chem. Ind.* (Milan) 42, 255 (1960), and later confirmed by Zambelli et al, *Makromol. Chem.* 112, 183 (1968).

A close examination of the above figures (I) and (II) for points of steric interactions between the olefin side chain and the attached polymer chain leads to a conclusion that the overall steric influences are much greater for primary addition than for secondary addition. This steric difference manifests itself in several ways: (1) a lower relative reactivity of substituted olefins in the primary addition mode (higher copolymerization r values for titanium versus vanadium), and (2) a higher temperature at which chain-end controlled isotacticity ($-10°$ C.) can be achieved relative to chain-end controlled syndiotacticity ($-60°$ C.).

If the metal and its ligands (L) are achiral in these figures, the only chirality which develops during the insertion step is due to the chiral carbons along the polymer chain itself. In isotactic stereoblock and syndiotactic polymerization it is this rather weak chirality that directs the new monomer to one of two possible orientations relative to the polymer chain's last added monomer during insertion. Regardless of the fact that the growing chain can rotate freely and shift among the vacant coordination sites of the metal, the last added monomer, in each case, will exert an orienting effect on an olefin seeking coordination. If this orientation energy is large compared to the randomizing effects of kT, it can be shown with models that a tactic polymer will result. It can be shown, in fact, that an isotactic polymer will result from primary addition.

Although every second carbon of the polymer backbone of a growing poly-α-olefin chain is chiral, it has been shown in many different experiments that the effect of this chain chirality is not sensed beyond three bonds separation from the metal as reported in Zambelli et al, *Macromolecules*, v. 16, pp. 341-8 (1983). In addition, adequate chirality for tactic propagation may not be sensed when the differences between the groups forming the chiral center become smaller. Such effects can be quite profound. Propylene, which introduces a chiral carbon center bonded to a hydrogen, a methyl group, and a polymer chain, is the only α-olefin which is readily polymerized by the chain-end control mechanism to an isotactic stereoblock and a syndiotactic polymer. For higher α-olefins, the larger steric bulk of the olefin branch and its similarity to the polymer chain causes polymerization rates and/or stereoregularity to be severely depressed.

Heretofore, the most effective way to produce isotactic poly-α-olefins from metallocene-alumoxane catalysts has been to use a metallocene which has chirality centered at the transition metal as reported in Ewen, J. A., *J. Amer. Chem. Soc.*, v. 106, p. 6355 (1984) and Kaminsky, W., et al, *Angew. Chem. Int. Ed. Eng.*; 24, 507-8 (1985). The best known conventional Ziegler-Natta catalyst which polymerizes olefins to normal isotactic structures, $TiCl_3$, also has metal centered chirality which the titanium acquires by being located at specific edge and defect sites on the crystal lattice. Both titanium and zirconium metallocenes containing a 1,2-ethylene bridged indenyl (or a tetra-hydroindenyl) ligand in the racemic form are good examples of such chiral metallocene catalysts which produce poly-olefins of the normal isotactic structure. The asymmetric steric environment of the metal in each of these catalysts induces a reproducible orientation of the incoming monomers, which is a mechanistic requirement in addition to CIS primary addition that must be met by a catalyst in order to polymerize stereoregularly. When catalyst site chirality is unchanging and primary addition occurs, normal isotactic polymers result.

FIGS. 1–4 demonstrate for TiCl₃ and for two chiral forms and one non-chiral form of metallocenes how metal centered chirality can direct isotactic polymerization. In FIG. 1 a titanium trichloride center which is complexed to a dialkyl aluminum chloride and a growing polymer chain is represented. The chirality contributed by the crystalline TiCl₃ site alone has been reputed to be of foremost importance in this mechanism in Natta, *J. Inorg. Nucl. Chem.* 8, 589 (1958). While additional chirality contributed by coordinated aluminum alkyls, bound chiral polymer chains, and added third components has been reported to produce observable effects in Boor, Langer and Zambelli et al (1983) mentioned above, these act primarily to enhance the isotacticity by increasing the steric bulk around the site. Generally such 'modifiers' simultaneously decrease the polymerization rate at a site as they increase its isotacticity.

In FIG. 1, a vacant monomer coordination site is indicated by the open square. Monomer coordination at this site occurs only with the olefin branch pointing in one direction due to severe steric interactions in the other configuration. If the polymer chain Pn were to shift to the vacant position, monomer coordination must occur in the opposite configuration at the newly opened vacant site. Sites of both chiral configurations, created by a shift in the position of the polymer chain, as implied above, are thought not to occur in crystalline TiCl₃ systems as reported in Langer, mentioned above. In these systems, the two sites clearly do not have equivalent steric and electronic requirements.

Chiral metallocenes which polymerize alpha-olefins to normal isotactic polymers have many structural similarities to the crystalline titanium catalysts. In these soluble metallocene-alumoxane catalysts, however, chirality is imposed on the metal center by the asymmetric metallocene ligand, rather than by a crystalline lattice of chloride ions. FIG. 2 shows the R and S (mirror image) forms of the racemic 1,2-ethylene bridged bis-tetra-hydroindenyl zirconium (IV) catalyst reported in wild et al, *J. Organomet. Chem.* 232, 233–47 (1982) and Ewen and Kaminsky, mentioned above. FIG. 3 indicates how the monomer, on binding, is oriented by the chiral projections of the ligand. Both of the racemic indenyl catalyst structures satisfy all the criteria for stereoregular polymerization, including that shifting the polymer chain to the opposite coordination vacancy causes the catalyst to direct the monomer to bind in the opposite configuration. This criterion, thought not to be applicable to titanium chloride catalysts, may have greater importance for these metallocene catalysts since the two coordination sites where the polymer and monomer bind should be equivalent sterically and electronically.

The structure shown in FIG. 4, a bridged tetrahydroindenyl isomer, is achiral since it has a plane of symmetry which intersects the metal atom between the planes of the metallocene rings. As expected, this meso isomer does not orient the monomer at either coordination vacancy and, as a result, does not polymerize stereoregularly by the catalyst site control mechanism. The chain end control mechanism would still enable this catalyst to form isotactic stereoblock polymer by the chain-end control mechanism under conditions described in U.S. Pat. No. 4,522,482.

Topping the list of metallocene structures which have been shown to polymerize stereoregularly are the ethylene bridged bis-indenyl and bis-tetra-hydroindenyl titanium and zirconium (IV) catalysts discussed above. These catalyst structures were synthesized and studied in Wild et al (1982) mentioned above, and were later reported in Ewen and Kaminsky et al, mentioned above, to polymerize α-olefins stereoregularly when combined with alumoxanes. It was further disclosed in West German Off. DE 3443087A1 (1986) without giving experimental verification, that the bridge length can vary from a $C_1$ to $C_4$ hydrocarbon and the metallocene rings can be simple or bicyclic but must be asymmetric.

Another type of catalyst chirality is formed by arranging non-chiral ligands in a chiral manner around the catalytic metal center. Many chiral complexes of this type can be mentally formulated in a short time; however, since none of these structures have induced isotacticity in poly-α-olefins as far as the applicant is aware, only a few reported structures will be mentioned here, including those structures the stereoregulating ability of which has been tested. The failure of these structures to polymerize stereoregularly must indicate that their site chirality is either lost in the active state of the catalyst, such as might happen in a three-coordinate cationic intermediate, or is insufficient to orient the monomer. Martin et al, *J. Organomet. Chem.* 97, 261–273 (1975) and Couturier et al, *J. Organomet. Chem.* 195, 291–306 (1980), have reported the preparation of a large number of titanium and zirconium derivatives of this type as follows:

| Metallocene | Tacticity |
| --- | --- |
| (CpMe₅) Cp Zr Me Cl | No isotactic PP observed |
| (CpR) Cp Zr Et Cl | " |
| (CpR) (CpR') Zr Me Cl | " |
| (CpMe₅) Cp Ti (C₆F₅) Cl | " |
| (Indenyl) Cp Zr Me Cl | " |

Metallocenes which are chiral but do not contain a bridge can be synthesized by introducing a chiral group into one of the ligands. In these examples, one of the ligands rather than the metal is the 'center' of the chirality. The resultant complexes have non-superimposible mirror images and thus are chiral and exist as R and S isomers. This type of chirality will not be lost in a three-coordinate intermediate provided that the chiral ligand is not lost. Martin et al and Couturier et al mentioned above have also reported preparation of numerous compounds of this structure. The following compounds contain this type of chirality, but have not been shown to have the ability to polymerize propylene stereoregularly:

| Metallocene* | Tacticity |
| --- | --- |
| rac-(methyl H₄-Indenyl)₂ Zr Cl₂ | No isotactic PP observed |
| (R,S) Cp₂ Zr (isobutyl) Cl | " |
| (R'Cp) Cp Zr Cl₂ | " |
| (R'CP)₂ Zr Cl₂ | " |

*Rt = —CH₂CH(CH₃)(C₆H₅)
—CH(CH₃)(C₂H₅)
—CH(CH₃)(C₆H₅)

It can thus be seen that there is a need for a catalyst which polymerizes α-olefins to high isotacticity with a minimum of inversions, is easily made in high yield and easily separated from meso forms thereof, and is capable of being tailored to meet the needed requirements of polymerization activity and isotacticity.

SUMMARY OF THE INVENTION

The present invention provides a silicon-bridged metallocene catalyst. The racemic isomers of the catalyst polymerize α-olefins to high isotacticity with a minimum of inversions and can be tailored to high activity and isotacticity. In addition, the catalyst is easily made in high yield and separated from meso forms.

In a broad aspect, the invention provides a chiral transition metal compound which has the formula:

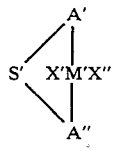

in which M' is a transition metal, X' and X" are the same or different hydride, halogen, hydrocarbyl or halohydrocarbyl having up to about 6 carbon atoms; A' and A" are the same or different asymmetrical mononuclear or polynuclear hydrocarbyl or silahydrocarbyl moieties; and S' is a silicon-containing bridge of 1–4 atoms selected from silanylene, silaalkylene, oxasilanylene and oxasilaalkylene.

In another aspect, the invention provides a catalyst system including (i) a silicon-bridged chiral metallocene of the formula:

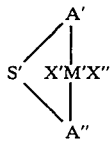

in which M' is a transition metal, X' and X" are the same or different hydride, halogen, hydrocarbyl or halohydrocarbyl having up to about 6 carbon atoms; A' and A" are the same or different asymmetrical mononuclear or polynuclear hydrocarbyl or silahydrocarbyl moieties; and S' is a silicon-containing bridge of 1–4 atoms selected from silanylene, silaalkylene, oxasilanylene and oxasilaalkylene; and (ii) an alumoxane selected from cyclic alumoxanes of the formula $(R-Al-O)_n$ and linear alumoxanes of the formula $R(R-Al-O)_nAlR_2$, wherein each R is independently $C_1$–$C_5$ alkyl and n is an integer from 2 to about 25. The metallocene-alumoxane catalyst dan be usefully supported on a catalyst support material.

DESCRIPTION OF THE PREFERRED EMBODIMENTS

Figure 1:
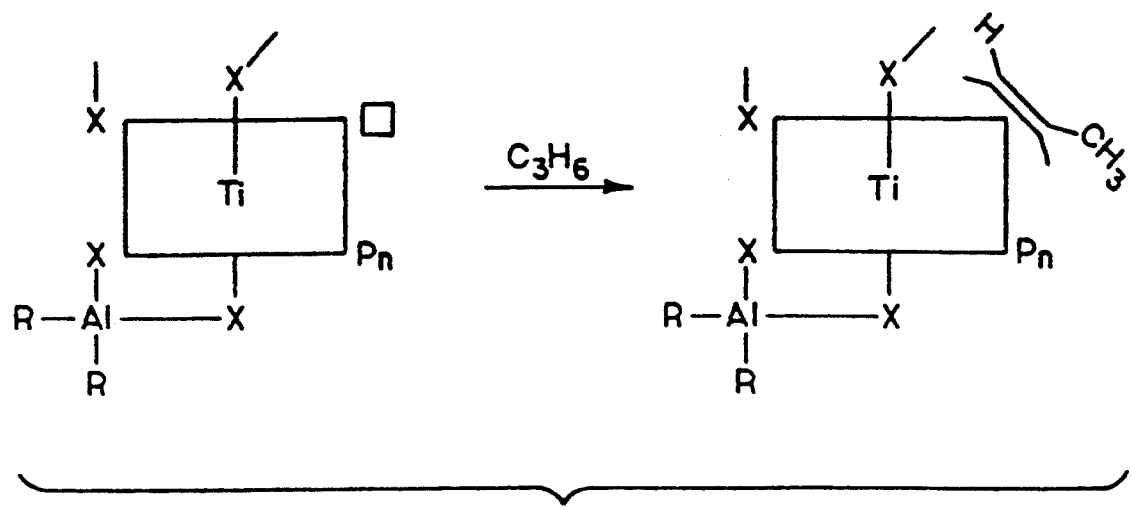
FIG. 1 (prior art) is a schematic representation of the polymerization of propylene with titanium trihalide complexed with dialkyl aluminum halide in which R represents alkyl and X represents halide.
Figure 2:
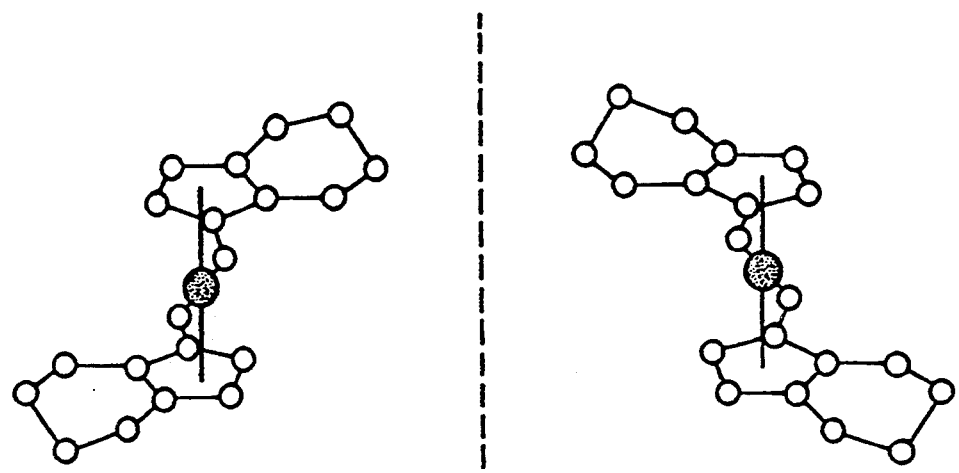
FIG. 2 (prior art) is a representation of the R and S forms of n-(1,1'-ethylene-bis(4,5,6,7-tetrahydroindenyl) zirconium.
Figure 3:
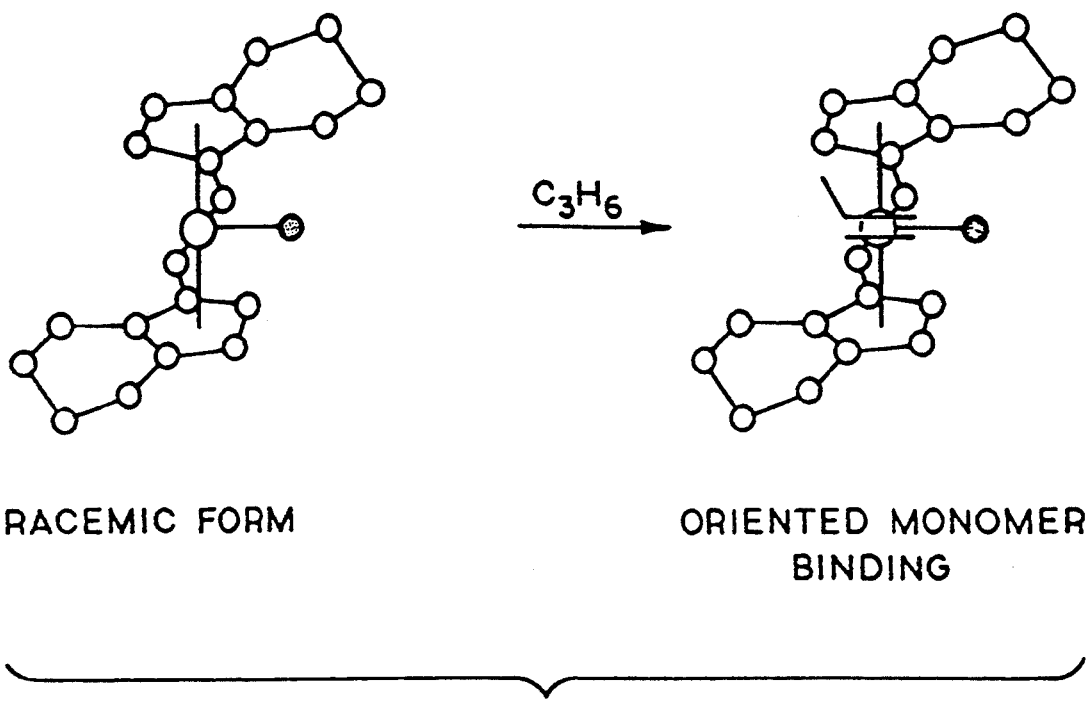
FIG. 3 (prior art) is a schematic illustration of monomer orientation with the zirconocene of FIG. 2.
Figure 4:
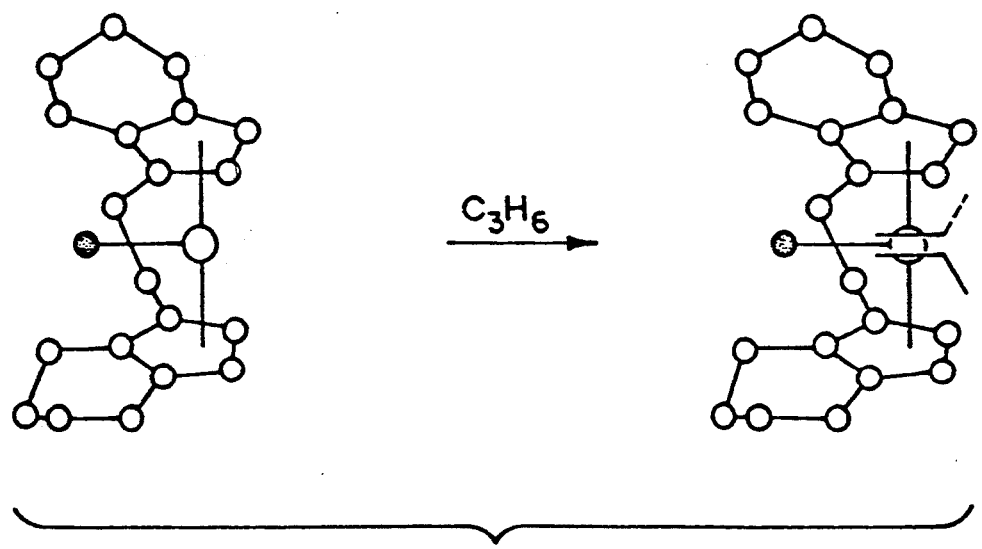
FIG. 4 (prior art) illustrates monomer binding of the meso form of n-(1,1'-ethylene-bis(4,5,6,7-tetrahydroindenyl) zirconium.
Figure 5:
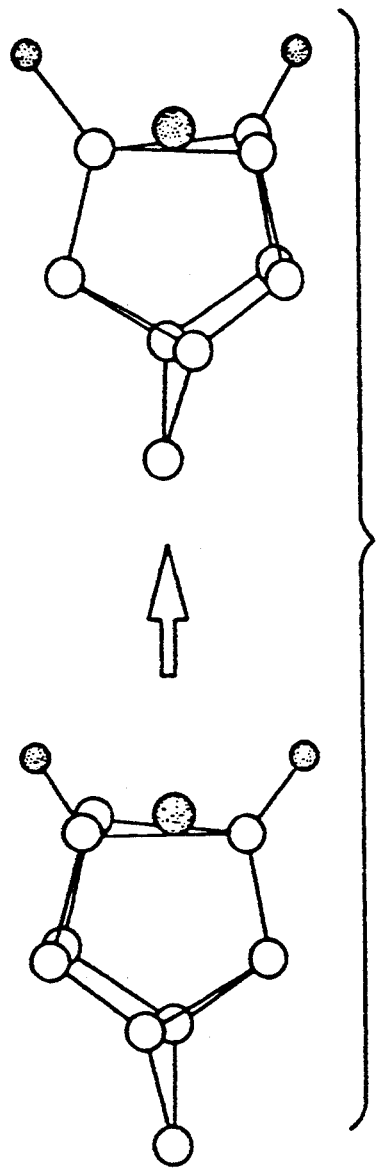
FIGS. 5–8 (prior art) illustrate the mobility of the chiral methyl groups of $C_1$–$C_4$ bridged his (methylcyclopentadienyl) zirconocenes with respect to the metal atom.
Figure 6:
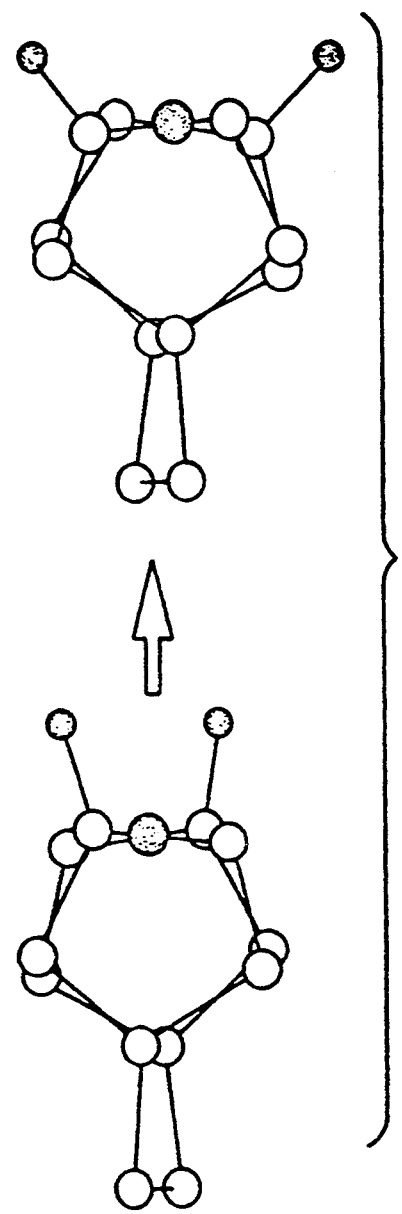
Figure 7:
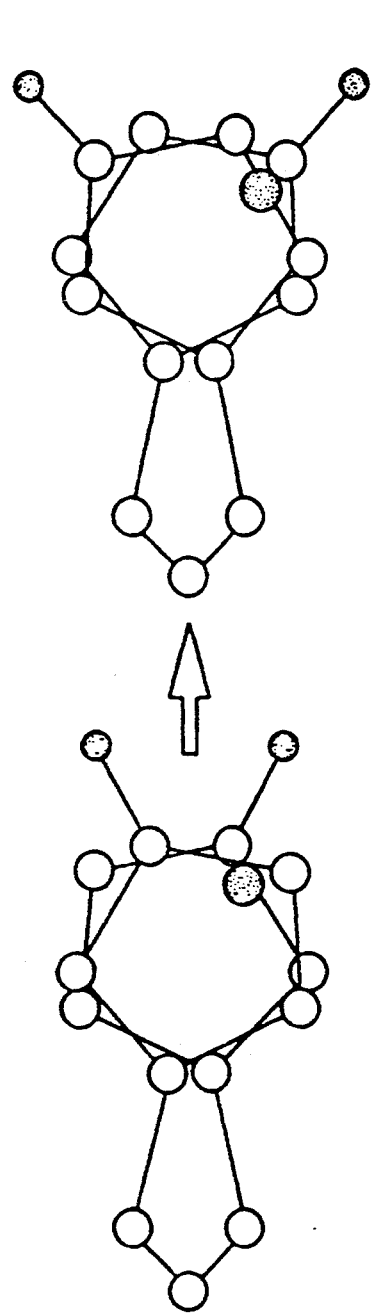
Figure 8:
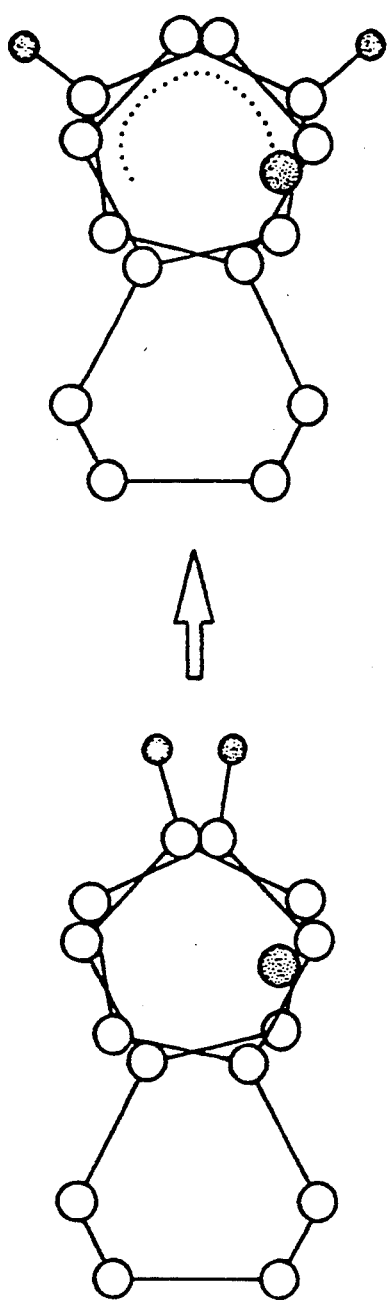

The silicon-bridged metallocene compounds of the invention have the general formula:

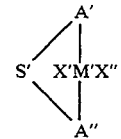

in which M' is a transition metal, X' and X" are the same or different hydride, halogen, hydrocarbyl or halohydrocarbyl having up to about 6 carbon atoms; A' and A" are the same or different asymmetrical mononuclear or polynuclear hydrocathyl or silahydrocarbyl moieties; and S' is a silicon-containing bridge of 1–4 atoms selected from silanylene, silaalkylene, oxasilanylene and oxasilaalkylene.

The transition metal M' in the above formula may be any transition metal, preferably a group IVB transition metal. Exemplary preferred transition metals include titanium, hafnium and especially zirconium.

As mentioned above, the transition metal substitutents X' and X" may be the same or different and are selected from hydride, alkyl, aryl, halogen, haloakyl, and haloaryl. X' and X" are preferably halogen or $C_1$–$C_6$ alkyl. Exemplary substituents include hydride, methyl, ethyl, propyl, butyl, pentyl, hexyl, cyclohexyl, phenyl, chloride, bromide, fluoride, iodide, and the like.

A' and A" may be any mononuclear or polynuclear hydrocarbyl or silahydrocarbyl which is asymmetric. Preferably, A' and A" have the formula:

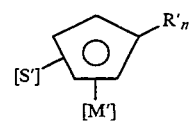

wherein n is an integer from one to four and each R' is the same or different hydrocarbyl or silahydrocarbyl, preferably of 1–20 carbon atoms and 0–2 silicon atoms, or taken together, two or more of R' are hydrocarbylene or silahydrocarbylene, preferably of 1–20 carbon atoms and 0–2 silicon atoms. As representative examples of R' there may be mentioned methyl, ethyl, butyl, propyl, hexyl, octyl, decyl, dodecyl, silyl, trimethyl silyl, propylene, butylene, butenylene, pentylene, pentenylene, hexylene, hexenylene, hexadienylene, phenyl, phenylene, and the like. Particularly preferred A' and A" hydrocarbyls and silahydrocarbyls include methylcyclopentadienyl, indenyl, 4,5,6,7 tetrahydroindenyl, and trimethylsilanylcyclopentadienyl.

S' is a bridge having a chain length of 1–6 atoms, preferably 1–4 atoms, and especially 1–3 atoms. The bridge must contain at least one silicon atom, but may be composed entirely of silicon atoms. The bridge atoms may also include 0–2 oxygen atoms and 0–4 carbon atoms. The silicon and carbon atoms may be unsubstituted or substituted with 1–2 alkyl, silanyl or silaalkyl groups which may be the same or different. Preferably, the silicon atoms are disubstituted with alkyl groups. Thus, preferred bridges include dialkylsilanylene[R$_2$Si=], 1-sila-1,1-dialkylethylene [—SiR$_2$CH$_2$—], tetraalkyldisilanylene [—SiR$_2$—SiR$_2$—], 2-sila-2,2-dialkylpropylene [—H$_2$C—SiR$_2$—CH$_2$—], 1,3-disila-1,1,3,3-tetraalkylpropylene [—SiR$_2$—CH$_2$—R$_2$Si—], dialkylsiloxy (dialkyl) silanylene [—R$_2$SiO—SiR$_2$—], 1,4-disila-1,1,4,4-tetraalkylbutylene [—SiR$_2$—CH$_2$—CH$_2$—SiR$_2$—]. Specifics representative examples include dimethylsilanylene, tetramethyldisilanylene, hexamethyltrisilanylene, 1-sila-1,1-dimethylethylene, 2-sila-2,2-dimethylpropylene, 1,3-disila-1,1,3,3-tetramethylpropylene, dimethylsiloxy (dimethyl) silanylene, 1,4-disila-1,1,4,4-tetramethylbutylene and the like.

It is critical for catalytic stereospecificity in olefin polymerization that these metallocene catalyst be chiral. It is also important that the degree of rotational restriction of the metallocene portion of the catalyst be somewhat limited, and that the non-metallocene binding sites be constant relative to the metallocene binding site. This is generally achieved by the silicon-containing bridges of the present catalyst. For example, the ring centroid-metal-ring centroid angle for dimethylsilanyl bridged bis(4,5,6,7-tetrahydroindenyl) zirconium chloride is 126.4 degrees. However, the same angle for the corresponding ethylene bridged metallocene is 125.0 degrees, suggesting that the silicon bridge is less restrictive than the two-carbon ethylene bridge. Quite surprisingly, the silicon bridged metallocene polymerizes with a higher stereoregularity than the ethylene bridged analogue.

The effects of the ring rotational flexibility on the mobility of chiral groups relative to the metal atom are illustrated in FIGS. 5–8 for $C_1$–$C_4$ bridged bis(methylcyclopentadienyl) metallocenes. It is seen that generally, with carbon bridges, the mobility, and hence the incidence of inversions in stereoregular polymerization, increases with the bridge length. With $C_4$ bridges, it is expected that a fairly high proportion of the polymer obtained with metallocenes containing them will be atactic. Additionally, as disclosed in Soga et al., *Makromol. Chem., Rapid Commun.* 8, 305–310 (1987), ethylene bridged tetrahydroindenyl zirconium catalysts introduce 1-3 insertion of the monomer.

Preferred metallocene catalysts according to the present invention include: racemic [1,1'-dimethylsilanylene-bis(3-methylcyclopentadienyl)] zirconium dichloride; [1,1'-dimethylsilanylene-bis(indenyl)] zirconium dichloride; [1,1'-dimethylsilanylene-bis(4,5,6,7-tetrahydroindenyl)] zirconium dichloride; [1,1'-(1,1,2,2-tetramethyldisilanylene)-bis(3-methylcyclopentadienyl)] zirconium dichloride; [1,1'-(1,1,2,2-tetramethyldisilanylene)-bis(4,5,6,7-tetrahydroindenyl)] zirconium dichloride; [1,1'-dimethylsilanylene-bis(3-trimethylsilanylcyclopentadienyl)] zirconium dichloride; [1,1'-(1,1,2,2-tetramethyldisilanylene)-bis(3-trimethylsilanylcyclopentadienyl)] zirconium dichloride; [1,1'-(1,1,3,3-tetramethyldisiloxanylene)-bis(4,5,6,7-tetrahydroindenyl)] zirconium dichloride; [1,1'-(1,1,4,4-tetramethyl-1,4-disilanylbutylene)-bis(4,5,6,7-tetrahydroindenyl)] zirconium dichloride; [1,1'-(2,2-dimethyl-2-silapropylene)-bis(3-methylcyclopentadienyl)] zirconium dichloride.

Preferred metallocene catalysts according to the present invention also include: racemic [1,1'-dimethylsilanylene-bis(3-methylcyclopentadienyl)] hafnium dichloride; [1,1'-dimethylsilanylene-bis(indenyl)] hafnium dichloride; [1,1'-dimethylsilanylene-bis(4,5,6,7-tetrahydroindenyl)] hafnium dichloride; [1,1'-(1,1,2,2-tetramethyldisilanylene)-bis(3-methylcyclopentadienyl)] hafnium dichloride; [1,1'-(1,1,2,2-tetramethyldisilanylene)-bis(4,5,6,7-tetrahydroindenyl)] hafnium dichloride; [1,1'-dimethylsilanylene-bis(3-trimethylsilanylcyclopentadienyl)] hafnium dichloride; [1,1'-(1,1,2,2-tetramethyldisilanylene)-bis(3-trimethylsilanylcyclopentadienyl)] hafnium dichloride; [1,1'-(1,1,3,3-tetramethyldisiloxanylene)-bis(4,5,6,7-tetrahydroindenyl)] hafnium dichloride; [1,1'-(1,1,4,4-tetramethyl-1,4-disilanylbutylene)-bis(4,5,6,7-tetrahydroindenyl)] hafnium dichloride; [1,1'-(2,2-dimethyl-2-silapropylene)-bis(3-methylcyclopentadienyl)] hafnium dichloride.

The silicon bridged metallocenes of the present invention are generally prepared by first building the ligand structures through simple alkylation/silanylation steps, and then inserting the transition metal using the metal tetrahalide. Lithium and sodium alkyls are preferably used for alkylation/silanylation. This is in contrast to Grignard reagents which must generally be employed for alkylene bridges, such as in the preparation of 1,2-ethylene bridged metallocenes, to obtain reasonable yields of the alkylene bridged metallocenes. For example, indene or cyclopentadiene are reacted with alkyllithium such as methyllithium or butyllithium, in a suitable solvent, such as tetrahydrofuran, to form the corresponding alkyllithium indenide or cyclopentadienide. If an alkylated ligand is desired, the alkyllithium compound can then be reacted with a corresponding alkylhalide to yield the alkylated ligand. For example, n-butylchloride may be reacted with lithium indenide to yield n-butyl indene, and methylchloride with lithium cyclopentadienide to yield methylcyclopentadiene. Silanylation may be accomplished in an analogous manner, such as by reacting trimethylchlorosilane with lithium cyclopentadienide to yield trimethylsilanyl cyclopentadiene.

Bridge formation also preferably employs alkyllithium or sodium intermediates rather than Grignard reagents. For example, dimethylsilanylene bridges are formed by the reaction of lithium indenide, methylcyclopentadienide or trimethylsilanylcyclopentadienide, with dimethyldichlorosilane; and 2-sila-2,2-dimethylpropylene bridges by the reaction of lithium indenide, methylcyclopentadienide or trimethylsilanylcyclopentadienide, with di(chloromethyl) dimethylsilane. The bridge formation may also be completed before alkylation/silanylation, as the order thereof is not generally critical.

Following formation of the desired silicon bridged ligand structure, the metallocene is formed by reaction of the lithium or sodium salt of the ligand structure with the transition metal halide, for example, zirconium or hafnium tetrachloride. The racemic form may then generally be readily separated from the meso form by crystallization from a solvent such as methylene dichloride using a hydrocarbon diluent, e.g. pentans, as an antisolvent, and recovering the crystallized racemic metallocene by filtration from the solution in which the meso metallocene generally remains soluble.

The silicon bridged metallocenes described herein generally have utility in stereoregular polymerization of α-olefins. The metallocenes may be used alone, but preferably are complexed with an alumoxane cocatalyst of the formulae $(R'''-Al-O)_p$ for cyclic alumoxanes, or $R'''(R'''-Al-O)_qAlR_2''$ for linear alumoxanes, in which $R'''$ is $C_1$–$C_5$ alkyl, for example, methyl, ethyl, propyl, butyl or pentyl, and p and q are integers from 2 to about 25. Most preferably, $R'''$ is methyl and p and q are at least 4. Alumoxanes can be prepared by various procedures known in the art. For example, an aluminum alkyl may be treated with water contained in a moist inert organic solvent, or it may be contacted with a hydrated salt, such as hydrated ferrous sulfate suspended in an inert organic solvent, to yield an alumoxane. Generally, however prepared, the reaction of an aluminum alkyl with a stoichiometric amount of water yields a mixture of the linear and cyclic species of the alumoxane.

The catalyst desirably is in a form of a complex formed upon admixture of the metallocene as specified with an alumoxane. The catalyst complex may be prepared as a homogeneous catalyst by addition of the requisite metallocene and alumoxane to the solvent in which polymerization will be carried out by solution polymerization procedures. The catalyst complex can also be prepared and employed as a heterogeneous catalyst by adsorbing and complexing the requisite silicon bridged metallocene and alumoxane components on a catalyst support material, such as silica gel, alumina or other inorganic support material. When prepared in heterogeneous or supported form, it is preferred to use silica gel as the support material. The heterogeneous form of the catalyst complex is generally employed in a suspension or slurry polymerization procedure with or without additional alumoxane present in the liquid phase. In the preparation of poly-α-olefins, it is preferred to utilize the α-olefin monomer in liquified state as the polymerization diluent.

The support material for preparing a heterogeneous catalyst may be any finely divided inorganic solid porous support, such as talc, silica, alumina, silica-alumina and mixtures thereof. Other inorganic oxides that may be employed either alone or in combination with silica or silica-alumina are magnesia, titania, zirconia, and the like. The preferred support material is a silica gel.

The metallocene and alumoxane may be utilized in olefin polymerization in the form of a heterogeneous supported catalyst by deposition on a support material, such as silica gel. While it should not be construed that the invention is limited in any way by the following mechanistic interpretation, it is considered that for optimal effectiveness of the deposited alumoxane, it is desirable that the unbound water initially present on the undehydrated silica should be essentially wholly removed, while retaining a portion of surface hydroxyl groups which are capable of reacting with the alumoxane and bonding it to the silica surface. The silica gel may be prepared in dehydrated form by heating or otherwise treating it to remove its water content so as to convert same to a derivate which is clement to the formation the metallocene alumoxane catalyst complex. A suitable silica gel would have a particle diameter in the range 10–600 microns, preferably 30–100 microns; a surface area of 50–1000 $m^2/g$, preferably 100–500 $m^2/g$; and a pore volume of 0.5–3.5 $cm^3/g$. The silica gel may be heat treated at 100°–1000° C., preferably 200°–800° C. for a period of 1–100 hours, preferably 3–24 hours, to ensure removal of unbound water from its surfaces.

The order of addition of the metallocene and alumoxane to the support material can vary. For example, the metallocene (dissolved in a suitable hydrocarbon solvent) can be first added to the support material followed by the addition of the alumoxane; the alumoxane and metallocene can be added to the support material simultaneously; the alumoxane can be first added to the support material followed by the addition of the metallocene.

The treatment of the support material, as mentioned above, is conducted in an inert solvent. The same inert solvent or a different inert solvent can be employed to dissolve the metallocene and alumoxanes. Preferred solvents include mineral oils and the various hydrocarbons which are liquid at reaction temperatures and in which the individual adsorbates are soluble. Illustrative examples of useful solvents include alkanes such as pentans, iso-pentane, hexane, hoptans, octane and nonane; cycloalkanes, such as cyclopentane and cyclohexane; and aromatics such as toluene, xylenes, ethylbenzene and diethylbenzene. The support material may be present by itself, which is preferred, or may be slurried in the inert solvent, and the metallocene and alumoxane are dissolved in the inert solvent prior to addition to the support material.

The supported catalyst is prepared by simply adding the adsorbates in a suitable solvent, preferably toluene, to the support material which is by itself or in a slurry. Preferably, a solution of the adsorbate is added to the dried support material. Most preferably, a toluene solution of the adsorbate is added to silica. In accordance with the preferred embodiment of this invention, the alumoxane dissolved in toluene is added to the silica particles in a first step, and the treated solid is dried. The dried solid is then treated with a solution in an inert solvent of the metallocene as a second step. In both of these steps, the conditions for addition of the adsorbates are not particularly critical. The adsorbates can be added to the reaction vessel rapidly or slowly. The amount of solvent to be employed is not critical. Nevertheless, the amount should be employed so as to provide adequate heat transfer away from the catalyst components during reaction and to permit good mixing. The temperature maintained during the contact of the reactants can vary widely, such as, from 0° to 100° C. Greater or lesser temperatures can also be employed. Preferably, the alumoxanes and metallocene are added to the silica at room temperature. The reaction between the alumoxane and the support material is rapid, however, it is desirable that the alumoxane be contacted with the support material for about one half hour up to eighteen hours or greater. Preferably, the reaction is maintained for about one hour.

At all times, the individual ingredients as well as the recovered catalyst components are protected from oxygen and moisture. Therefore, the reactions must be performed in an oxygen and moisture free atmosphere and recovered in an oxygen and moisture free atmosphere. Preferably, therefore, the reactions are performed in the presence of an inert dry gas, such as nitrogen. The recovered solid catalyst is maintained in a nitrogen atmosphere.

Upon completion of the reaction of the metallocene and alumoxane with the support, the solid material can be optionally treated with a small amount of monomer, e.g. ethylene, to prepolymerize the solid catalyst materials to a weight increase of from about 50 to about 1000% based on total weight of catalyst and support material. Then the solid material, as such or as prepolymerized, can be recovered by any well-known technique. For example, the solid catalyst material can be recovered from the liquid by vacuum evaporation or decantation. The solid is thereafter dried under a stream of pure dry nitrogen or dried under vacuum. Prepolymerization of the solid catalyst material aids in obtaining a polymer produced therefrom in well defined particle form.

The catalyst complex obtained through contacting of the metallocene and the alumoxane cocatalyst may be homogeneous, heterogeneous or supported and may be formed prior to introduction of these components into the reactor. The homogeneous catalyst may be formed in the reactor. The ratio of Al to transition metal can be in the range of 0.5–100,000, most desirably 1–1000. The preferred ratio of Al to metal is in the range 1–200, desirably 20–200. If desired, the heterogeneous and supported catalyst complex may be contacted with a small amount of a monomer, e.g. ethylene, in amounts such as to effect a weight gain of 50–1000% based on total weight of catalyst and support material, if employed. In this case, additional alumoxane cocatalyst may be used in the reactor so that the total ratio of Al to metal is in the range 1–5000, preferably 5–4000 and most preferably 10–1000. Likewise, in this case, a small amount of another aluminum compound may be added to the reactor together with, or instead of, additional alumoxane, for the purposes of scavenging any impurities which may be present in the reactor.

In accordance with a preferred procedure the metallocene-alumoxane catalyst complex may be used to produce isotactic poly-α-olefins by slurry polymerization utilizing the olefin monomer as the polymerization diluent in which a metallocene-alumoxane catalyst complex is dissolved in an amount sufficient to yield a polymer with the desired monomer content. If desired, comonomer is supplied to the polymerization diluent. Generally the polymerization process is carried out with a pressure of from about 10 to about 1000 psi, most preferably from about 40 to about 600 psi. The polymerization diluent is maintained at a temperature of from about $-10°$ to about 150° C., preferably from about 20° to about 100° C., and most preferably from about 30° to about 90° C. These catalysts may also be employed in a high temperature/pressure polymerization process. In such, the pressure can be in the range of 5,000–40,000 psi and the temperature in the range of 120°–300° C.

The polymerization may be carried out as a batchwise slurry polymerization or as a continuous process slurry polymerization. The procedure of continuous process slurry polymerization is preferred, in which event α-olefin and catalyst are continuously supplied to the reaction zone in amounts equal to the α-olefin and catalyst removed from the reaction zone with the polymer in the product stream.

The preparation of silicon bridged metallocenes of the present invention, and the use thereof as α-olefin polymerization catalysts, are illustrated by way of the examples which follow.

EXAMPLE 1

The compound 1,1'-dimethylsilanylene bridged bis-(indenyl) zirconium dichloride was prepared, and the racemic isomers thereof separated from the meso isomer. In a nitrogen atmosphere, 44 ml indene and 150 ml tetrahydrofuran (THF) were magnetically stirred in a one-liter flask. Carefully, 215 ml of methyllithium (1.4M in TBF) was added thereto with stirring at 0° C., and stirred for one hour. In another one-liter flask, 22.4 ml dimethyldichlorosilane and 150 ml THF were stirred, and the methyllithium indenide solution slowly added thereto at 25° C. over a one hour period. The mixture was stirred for one additional hour and then evaporated to one-half volume using a rotary evaporator. Carefully, 225 ml of methyllithium (1.4M in THF) was added thereto at 0° C. and the mixture stirred for one hour at 25° C.

Figure 9:
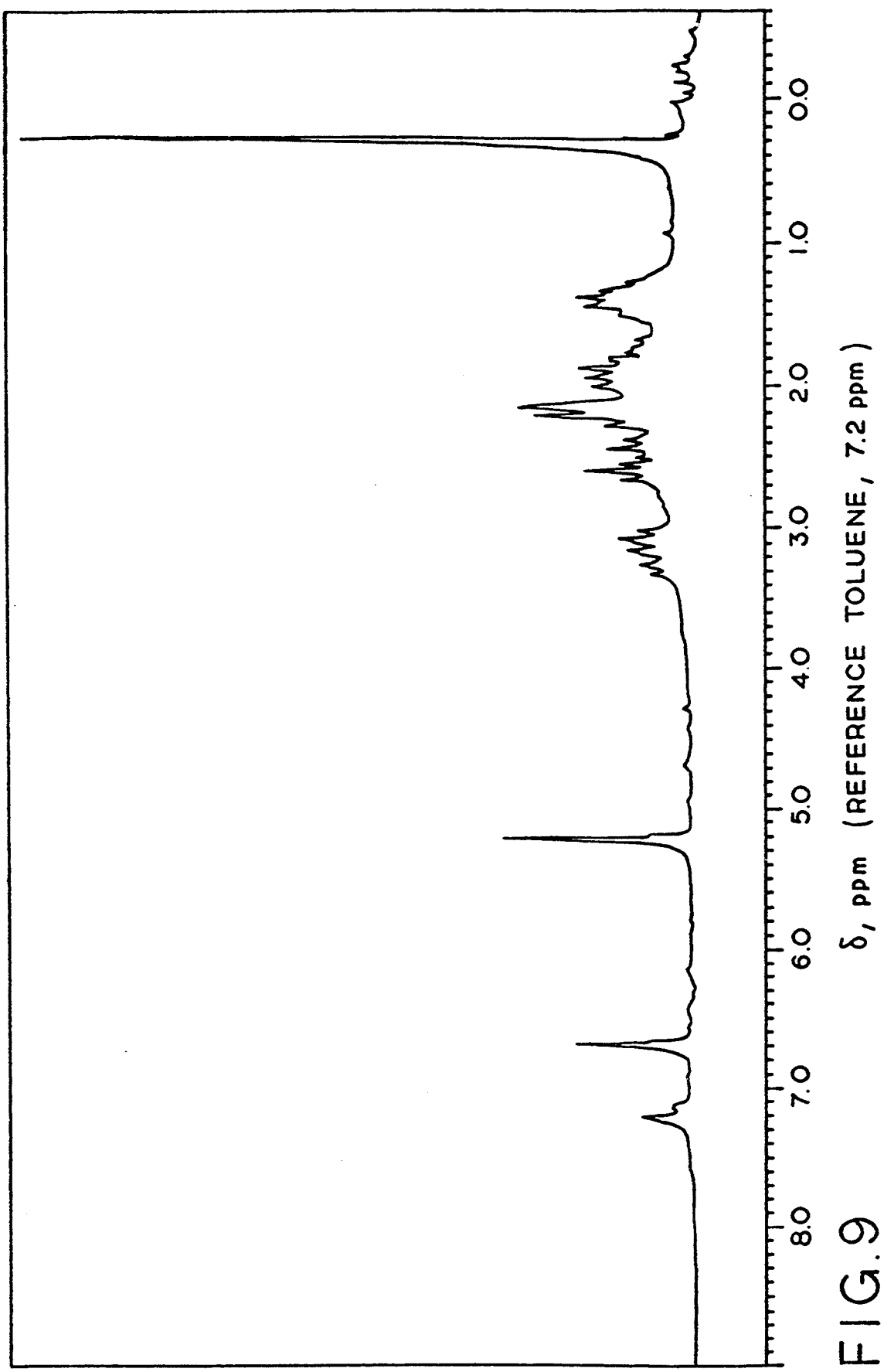
FIG. 9 is the H-1 NMR spectrum of racemic [1,1'-dimethylsilanylene-bis(4,5,6,7 tetrahyclroindenyl)] zirconium dichloride.
Figure 10:
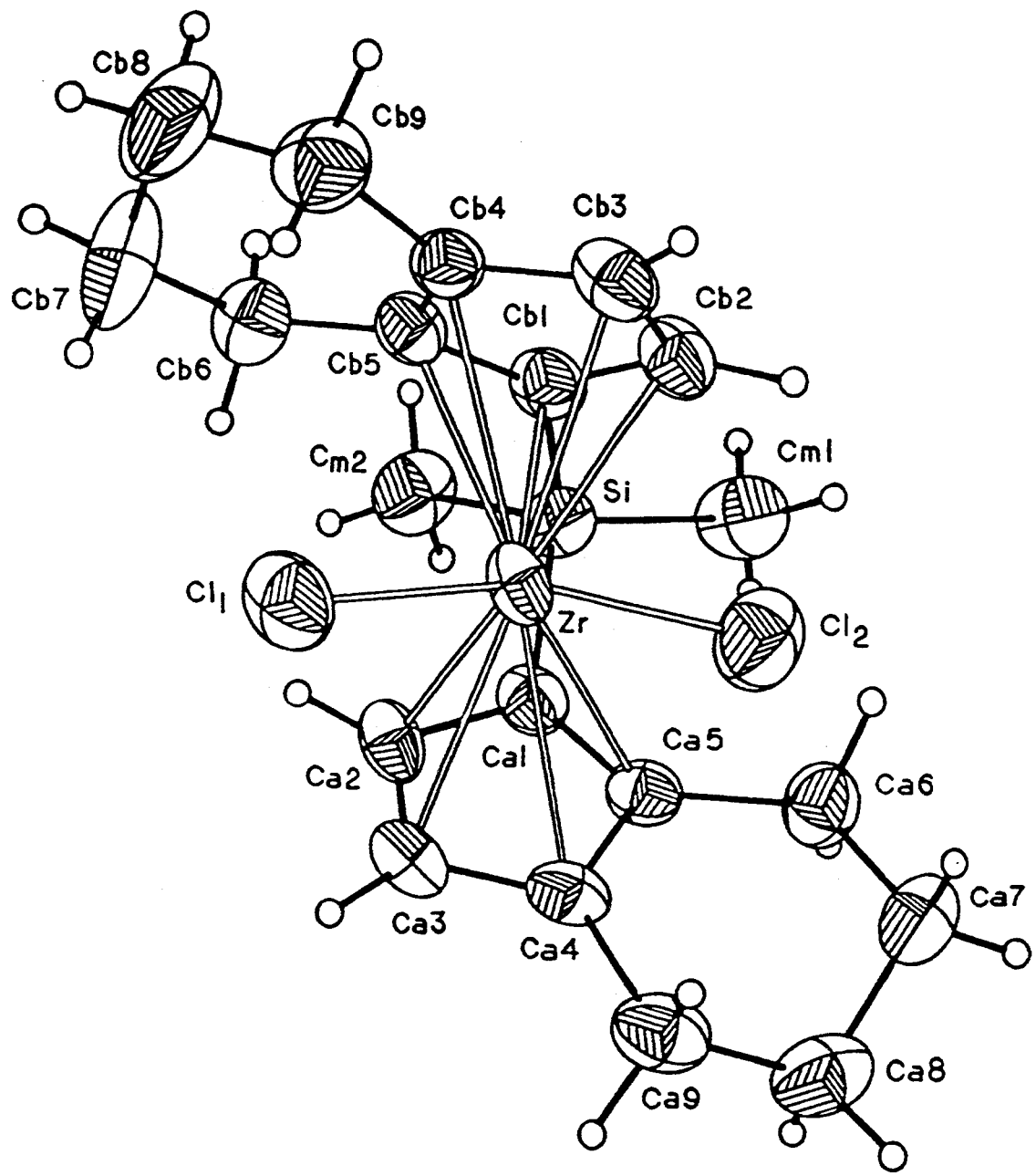
FIG. 10 is a representation of the crystalline structure of [1,1'-dimethylsilanylene-bis(4,5,6,7 tetrahydroindenyl)] zirconium dichloride.

In another one-liter flask, 200 cc THF was cooled to $-80°$ C. and 40 g of zirconium tetrachloride was slowly added with stirring. The stirring solution was allowed to warm to 25° C. The indene solution was slowly poured into the zirconium halide solution over a period of one hour at 25° C. and stirred overnight. The mixture was evaporated to an oil using a vacuum evaporator and allowed to stand for 24 hours. The oily mixture was filtered through a coarse glass frit to obtain the yellow crystalline, racemic bridged indene complex. The complex was washed with several 10 cc portions of THF which was at $-20°$ C. The meso isomer was obtained by extracting the vacuum evaporated filtrate with dichloromethane. To obtain the tetrahydroindenyl derivative, 200 cc of methylene chloride and 500 mg of platinum black or platinum (IV) oxide was added to the yellow racemic solid. This mixture was hydrogenated at 45° C. in a steel vessel using 600 psig hydrogen pressure for four hours. The resultant solution was filtered and evaporated to 100 cc or less. The insoluble racemic isomer was filtered off while the solution was slowly evaporated with cooling. The racemic isomer was thus crystallized in high purity. The yield was approximately 20 g of the racemic tetrahydroindenyl isomer. The crystal structure of this isomer is given in FIG. 10. The H-1 NMR spectrum of the racemic isomer in deuterobenzene, FIG. 9, showed the following main resonances:

singlet, 6H, 0.35δ
doublets, 4H, 5.2δ, 6.7δ
multiplets, 16H, 1.4δ, 1.9δ, 2.2δ, 2.6δ, 3.1δThe H-1 NMR spectrum of the racemic isomer in deuterobenzene prior to hydrogenation, $(CH_3)_2Si(indenyl)_2ZrCl_2$, showed the following resonances:
singlet, 6H, 0.55δ
doublets, 4H, 5.8δ, 6.8δ
multiplets, 8H, 6.8δ, 7.1–7.4δ

EXAMPLE 2

The compound 1,1'-dimethylsilanylene bridged bis(3-methylcyclopentadienyl) zirconium dichloride was prepared. In a nitrogen atmosphere, 28 g methylcyclopentadiene monomer and 150 cc tetrahydrofuran were magnetically stirred in a one-liter flask. 250 cc methyllithium (1.4M) was carefully added with stirring at 0° C. for one hour. In another one-liter flask, 22.6 g dimethyldichlorosilane and 150 cc THF were stirred, the lithium methylcyclopentadienide solution was slowly added to the silane solution at 25° C. over a one hour period and stirred for one additional hour. The solution was evaporated to one-half volume using a rotary evaporator, and then 250 cc of methyllithium (1.4M) at 0° C. was carefully added and stirred for one hour at 25° C. In another one-liter flask, 200 cc THF was cooled to $-80°$ C. and 40.8 g of zirconium tetrachloride was slowly added with stirring. The stirring solution was allowed to warm to 25° C. The lithium dimethylsilanyldi(methylcyclopentadienide) solution was slowly poured into the zirconium halide solution over a period of one hour at 25° C. and stirred 12 hours. The mixture was evaporated to an oil using a vacuum evaporator. The residue was extracted with hot hexane to dissolve the bridged metallocene dichloride $(CH_3)_2Si(CpMe)_2ZrCl_2$. The insoluble salts were filtered from the solution of metallocene. The hexane was cooled and evaporated to obtain 40 g of crystalline metallocene product which was stored in a dry, inert atmosphere. The H-1 NMR indicated that the product was a mixture of the meso and racemic isomers which could be separated by fractional crystallization from hexane. The NMR in deuterobenzene showed the following resonances:

Racemic and meso isomers:
  singlets, 12H, 0.2$\delta$, 2.3$\delta$
  multiplets, 6H, 5.0$\delta$, 5.2$\delta$, 5.4$\delta$, 5.6$\delta$, 6.5$\delta$, 6.6.$\delta$
Isolated racemic isomer:
  singlets, 12H, 0.2$\delta$, 2.3$\delta$
  multiplets, 6H, 5.0$\delta$, 5.6$\delta$, 6.6$\delta$

EXAMPLE 3

The compound 1,1'-dimethylsilanylene bridged bis(3-trimethylcyclopentadienyl) zirconium dichloride was prepared. In a nitrogen atmosphere, 48.4 g 2,4-cyclopentadien-1-yltrimethyl silane (Aldrich Chemical Co.) and 150 cc tetrahydrofuran in a one-liter flask were magnetically stirred. 250 cc methyllithium (1.4M) was carefully added with stirring at 0° C. for one hour. In another one-liter flask, 22.6 g dimethyldichlorosilane and 150 cc THF were stirred, and the lithium trimethylcyclopentadienide solution was slowly added to the dichlorosilane solution at 25° C. over a one hour period and stirred for one additional hour. The solution was evaporated to one-half volume using a rotary evaporator, and then 250 cc of methyllithium (1.4M) at 0° C. was carefully added and stirred for one hour at 25° C. In another one-liter flask, 200 cc THF was cooled to −80° C. and 40.8 g of zirconium tetrachloride was slowly added with stirring. The stirring solution was allowed to warm to 25° C. The ligand solution was slowly poured into the zirconium halide solution over a period of one hour at 25° C. and stirred overnight. The mixture was evaporated to an oil using a vacuum evaporator. The residue was extracted with hot hexane to dissolve the bridged metallocene dichloride $(CH_3)_2Si(Cp-Si(CH_3)_3)_2ZrCl_2$. The insoluble salts were filtered from the solution of metallocene. The hexane was cooled and evaporated to obtain 68 g of crystalline metallocene product which was stored in a dry, inert atmosphere. The H-1 NMR indicated that the product of the reaction was a mixture of the meso and racemic isomers which could be separated by fractional crystallization from hexane. The NMR in deuterobenzene showed the following resonances:

Racemic and meso isomers:
  singlets, 24H, 0.3$\delta$, 0.4$\delta$, 0.5$\delta$
  multiplets, 6H, 5.65$\delta$, 5.8$\delta$, 5.9$\delta$, 6.1$\delta$, 6.95$\delta$, 7.1$\delta$
Isolated racemic isomer:
  singlets, 24H, 0.3$\delta$, 0.5$\delta$:
  multiplets, 6H, 5.65$\delta$, 6.1$\delta$, 7.1$\delta$

EXAMPLE 4

The compound 1,1'-diethylsilanylene bridged bis(3-isobutylcyclopentadienyl) zirconium dichloride was prepared. In a nitrogen atmosphere, 42.7 g isobutylcyclopentadiene monomer and 150 cc tetrahydrofuran were magnetically stirred in a one-liter flask. Isobutycyclopentadiene monomer can be prepared by reacting sodium cyclopentadienide with isobutylbromide in THF at 40° C. for two hours. 250 cc methyllithium (1.4M) was carefully added with stirring at 0° C. for one hour. In another one-liter flask, 27.5 g diethyldichlorosilane and 150 cc THF were stirred, and the lithium isobutylcyclopentadienide solution was slowly added to the silane solution at 25° C. over a one hour period and stirred for one additional hour. The solution was evaporated to one-half volume using a rotary evaporator, and then 250 cc of methyllithium (1.4M) at 0° C. was carefully added and stirred for one hour at 25° C. In another one-liter flask, 200 cc THF was cooled to −80° C. and 40.8 g of zirconium tetrachloride was slowly added with stirring. The stirring solution was allowed to warm to 25° C. The ligand solution was slowly poured into the zirconium halide solution over a period of one hour at 25° C. and stirred overnight. The mixture was evaporated to an oil using a vacuum evaporator. The residue was extracted with hot hexane to dissolve the bridged metallocene dichloride $(CH_3-CH_2)_2Si(Cp-CH_2CH(CH_3)_2)_2ZrCl_2$. The insoluble salts were filtered from the solution of metallocene. The hexane was evaporated to obtain 52 g of the non-crystalline metallocene product which was stored in a dry, inert atmosphere. The H-1 NMR indicated that the product of the reaction was a mixture of the meso and racemic isomers. The NMR in deuterobenzene showed the following resonances:

Racemic and meso isomers:
  multiplet, 10H, 0.8$\delta$
  multiplet, 12H, 0.9$\delta$
  multiplet, 2H, 1.7$\delta$
  multiplet, 4H, 2.6$\delta$
  multiplet, 6H, 5.3–6.7$\delta$

EXAMPLE 5

A single stereoisomer of [1,1'-(2,2-dimethyl-2-silapropylene)-bis(3-trimethylsilanylcyclopentadienyl)] zirconium dichloride, $(CH_3)_2Si(CH_2)_2(C_5H_3Si(CH_3)_3)_2ZrCl_2$ was prepared and separated. In a nitrogen atmosphere, 100 cc distilled tetrahydrofuran, 28 cc of 1.8M sodium cyclopentadienide solution (THF), and 3.65 cc of di(chloromethyl)-dimethylsilane were combined and stirred for 24 hours at 35° C. 36 cc of 1.4M methyllithium at 0° C. was slowly added and allowed to warm to 25° C. while stirring for one hour. 6.4 cc of trimethylchlorosilane at 25° C. was added and stirred for one hour. 40 cc of 1.4M methyllithium at −20° C. was added, stirred and allow to warm to 25° C. The solution was cooled to −20° C. and 11 g of zirconium tetrachloride was slowly added. The solution was allowed to warm to 25° C. and stirred for 12 hours. The methylene dichloride was added and stirred. Dry HCl gas was bubbled into the solution for five minutes, then excess HCl was purged out by bubbling with nitrogen. The solution was filtered through a medium fritted glass filter. The solution was evaporated to 100 cc or less and cooled. Pentans was added, and the crystalline solid was separated. The filtrate may be concentrated to an oil to recover the other isomer. The yield was 6 grams of a crystalline isomer, possibly the racemic one, and 10 grams of an impure oil containing the other isomer. The crystalline leomar did not crystallize in a form adequate for x-ray structure determination. The H-1 NMR of the crystalline isomer in $CDCl_3$ showed the following resonances:

singlets, 24H, 0.3$\delta$, 0.4$\delta$
doublet, 2H, 5.85$\delta$
multiplets, 4H, 1.7$\delta$, 2.15$\delta$4H, 6.35$\delta$, 6.5–6.6$\delta$

Example 6

A tetramethylsilanylene bridged bis(methylcyclopentadienyl) zirconium dichloride was prepared. In a nitrogen atmosphere, 28 g methylcyclopentadiene monomer and 150 cc tetrahydrofuran (THF) were magnetically stirred in a one liter flask. 250 cc methyllithium (1.4M in THF) was added carefully with stirring at 0° C., and stirred for one hour. In another one liter flask, 32.9 g 1,1,2,2-tetramethyldichlorodisilane (Petrarch Chem. Co.) and 150 cc THF were stirred, and the lithium methylcyclopentadienide solution was slowly added to the silane solution at 25° C. over a one hour period. The mixture was stirred for one additional hour. The solution was evaporated to one-half volume using a rotary evaporator, and then 250 cc of methyllithium (1.4M) was carefully added at 0° C. This was stirred for one hour at 25° C.

In another one liter flask, 200 cc THF was cooled to −80° C. and 40.8 g of zirconium tetrachloride was slowly added with stirring. The stirring solution was allowed to warm to 25° C. The ligand solution was slowly poured into the zirconium halide solution over a period of one hour at 25° C., and stirred for 12 hours. The mixture was evaporated to an oil using a vacuum evaporator. The residue was extracted with hot hexane to dissolve the bridged metallocene dichloride $(CH_3)_4Si_2(C_5H_3CH_3)_2ZrCl_2$. This was filtered to separate the insoluble salts from the solution of metallocene. The hexane was cooled and evaporated to obtain 45 g of a semi-crystalline metallocene product. The product was stored in a dry, inert atmosphere. The H-1 NMR indicated that the product was a mixture of the meso and racemic isomers which were not separated. The NMR spectrum in deuterobenzene showed the following resonances:

Racemic and meso isomers:
 singlets, 12H, 0.25δ6H, 2.25δ, 2.35δ
 multiplets, 6H, 6.15δ, 6.35δ

Example 7

The compound tetramethyldisiloxane bridged bis(tetrahydroindenyl) zirconium dichloride was prepared. In a nitrogen atmosphere, 44 cc indene and 150 cc tetrahydrofuran were magnetically stirred in a one liter flask. 250 cc methyllithium (1.4M) were added with stirring at 0° C., and stirred for one hour. In another one liter flask, 35.5 g 1,3-dichlorotetramethyldisiloxane (Petrarch Chemical Co.) and 150 cc THF were stirred and the lithium idenide solution was slowly added to the siloxane solution at 25° C. over a one hour period. The mixture was stirred for one additional hour. The solution was evaporated to one-half volume using a rotary evaporator, and then 250 cc of methyllithium (1.4M) was carefully added at 0° C. The mixture was stirred for one hour at 25° C.

In another one liter flask, 200 cc THF was cooled to −80° C., and 40.8 g of zirconium tetrachloride was slowly added with stirring. The stirring solution was allowed to warm to 25° C. The ligand solution was slowly poured into the zirconium halide solution over a period of one hour at 25° C., and stirred 12 hours. The mixture was evaporated to an oil using a vacuum evaporator. The residue was extracted with dichloromethane to dissolve the bridged indene metallocene dichlorides $(CH_3)_4Si_2O(C_9H_6)_2ZrCl_2$, and filtered to separate the insoluble salts from the solution of metallocene. The dichloromethane was cooled and evaporated to obtain 45 g of a semi-crystalline metallocene product, which was stored in a dry, inert atmosphere.

To obtain the tetrahydroindenyl derivative, 200 cc of dichloromethane and 500 mg of platinum black or platinum (IV) oxide was added to the yellow semi-crystalline product. This mixture was hydrogenated at 45° C. in a steel vessel using 600 psig hydrogen pressure for four hours. The resultant solution was filtered and evaporated to 100 cc or less. The insoluble racemic isomer was filtered off while slowly evaporating the solution. The racemic isomer $[[(C_9H_{10})Si(CH_3)_2]_2O]ZrCl_2$, verified by single crystal x-ray determination, was thus crystallized in high purity. The H-1 NMR spectrum of the racemic isomer in deuterobenzene showed the following resonances:

singlets, 12H, 0.3δ
 doublets, 4H, 6.2δ, 6.6δ
 multiplets, 16H, 1.45δ, 2.0δ, 2.2δ, 2.55δ, 3.0δ

Example 8

The compound tetramethyldisiloxane bridged bis(cyclopentadienyl) zirconium dichloride was prepared. In a nitrogen atmosphere, 23.1 g cyclopentadiene monomer and 150 cc tetrahydrofuran were magnetically stirred in a one liter flask. 250 cc methyllithium (1.4M) was carefully added with stirring at 0° C., and stirred for one hour. In another one liter flask, 35.5 g [1,3-dichlorotetramethyldisiloxane] (Petrarch Chem. Co.) and 150 cc THF were stirred, and the lithium cyclopentadienide solution was slowly added to the silane solution at 25° C. over a one hour period. The mixture was stirred for one additional hour. The solution was evaporated to one-half volume using a rotary evaporator, and then 250 cc of methyllithium (1.4M) was carefully added at 0° C. This was stirred for one hour at 25° C.

In another one liter flask, 200 cc THF was cooled to −80° C., and 40.8 g of zirconium tetrachloride was slowly added with stirring. The stirring solution was allowed to warm to 25° C. The ligand solution was slowly poured into the zirconium halide solution over a period of one hour at 25 ° C., and stirred for 12 hours. The mixture was evaporated to an oil using a vacuum evaporator. The residue was extracted with hot hexane to dissolve the bridged metallocene dichloride $(CH_3)_4Si_2O(C_5H_4)_2ZrCl_2$. This was filtered to separate the insoluble salts from the solution of metallocene. The hexane was cooled and evaporated to obtain 42 g of a semi-crystalline metallocene product. The product was stored in a dry, inert atmosphere. The NMR spectrum in deuterobenzene showed the following resonances:

singlets, 12H, 0.3δ
 multiplets 8H, 6.35δ, 6.5δ

Example 9

The compound 1,1,4,4-tetramethyl-1,4-disilabutylene bridged his (methylcyclopentadienyl) zirconium dichloride was prepared. In a nitrogen atmosphere, 23.1 g cyclopentadiene monomer and 150 cc tetrahydrofuran were magnetically stirred in a one-liter flask. 250 cc methyllithium (1.4M) was carefully added with stirring at 0° C., and stirred for one hour. In another one-liter flask, 37.7 g 1,1,4,4-tetramethyl-1,4-dichlorodisilaethylene (Petrarch Chem. Co.) and 150 cc THF were stirred, and the lithium methylcyclopentadienide solution was slowly added to the silane solution at 25° C. over a one hour period. The mixture was stirred for one additional hour. The solution was evaporated to one-half volume using a rotary evaporator, and then 250 cc of methyllithium (1.4M) was carefully added at 0° C. This was stirred for one hour at 25° C.

In another one-liter flask, 200 cc THF was cooled to −80° C., and 40.8 g of zirconium tetrachloride was slowly added with stirring. The stirring solution was allowed to warm to 25° C. The ligand solution was slowly poured into the zirconium halide solution over a period of one hour at 25° C., and stirred for 12 hours. The mixture was evaporated to an oil using a vacuum evaporator. The residue was extracted with hot hexane to dissolve the bridged metallocene dichloride $(CH_2)_2(CH_3)_4Si_2(C_5H_4)_2ZrCl_2$. This was filtered to separate the insoluble salts from the solution of metallocene. The hexane was cooled and evaporated to obtain 55 g of a semi-crystalline metallocene product. The product was stored in a dry, inert atmosphere. The NMR spectrum in deuterobenzene showed the following resonances:
singlets, 12H, 0.15δ4H, 0.75δ
multiplets, 8H, 6.35δ, 6.45δ

Example 10

The compound dimethylsilanylene bridged bis(methylcyclopentadienyl) hafnium dichloride was prepared. In a nitrogen atmosphere, 28 g methylcyclopentadiene monomer and 150 cc diethylether were magnetically stirred in a one liter flask. 250 cc methyllithium (1.4M) was carefully added with stirring at 0° C. and stirred for one hour. In another one liter flask, 22.4 cc dimethyldichlorosilane 150 and 150 cc diethylether were stirred and the lithium methylcyclopentadienide solution was slowly added to the silane solution at 25° C. over a one hour period and stirred for one additional hour. The solution was evaporated to one-half volume using a rotary evaporator, and then 250 cc of methyllithium (1.4M) at 0° C. was carefully added and stirred for one hour at 25° C. The ether solvent was evaporated completely using a vacuum evaporator. 400 cc toluene and 56.0 g hafnium tetrachloride was added. The flask was attached to a reflux condenser and nitrogen bubbler, and the toluene solution was refluxed for 24 hours under a nitrogen atmosphere. The toluene solution was cooled to 25° C. and vacuum evaporated to dryness. The residue containing the metallocene complex was extracted from the unreacted salts by washing with 500 cc dichloromethane. The dichloromethane solution was evaporated to obtain 30 g of the racemic isomer, rac-$(CH_3)_2Si(C_5H_3CH_3)_2HfCl_2$, as a crystalline product. The H-1 NMR spectrum in deuterobenzene showed the following resonances:
isolated racemic isomers;
singlets, 12H, 0.25δ, 2.35δ
multiplets, 6H, 5.15δ, 5.7δ, 6.6δ
racemic and meso isomers;
singlets, 12H, 0.25δ, 2.35δ
multiplets, 6H, 5.1δ, 5.2δ, 5.4δ, 5.7δ, 6.5δ, 6.6δ

Example 11

The compound dimethylsilanylene bridged bis(indenyl) hafnium dichloride was prepared. In a nitrogen atmosphere, 44 cc indene and 150 cc diethylether were magnetically stirred in a one-liter flask. 250 cc methyllithium (1.4M) was carefully added with stirring at 0° C. and stirred for one hour. In another one-liter flask, 22.4 cc dimethyldichlorosilane 150 and 150 cc diethylether were stirred and the lithium indene solution was slowly added to the silane solution at 25° C. over a one hour period and stirred for one additional hour. The solution was evaporated to one-half volume using a rotary evaporator, and then 250 cc of methyllithium (1.4M) at 0° C. was carefully added and stirred for one hour at 25° C. The ether solvent was evaporated completely using a vacuum evaporator. 400 cc toluene and 56.0 g hafnium tetrachloride was added. The flask was attached to a reflux condenser and nitrogen bubbler, and the toluene solution was refluxed for 24 hours under a nitrogen atmosphere. The toluene solution was cooled to 25° C. and vacuum evaporated to dryness. The residue containing the metallocene complex was extracted from the unreacted salts by washing with 500 cc dichloromethane. The dichloromethane solution was evaporated to obtain 30 g of the racemic isomer, rac-$(CH_3)_2Si(C_9H_6)_2HfCl_2$, as a crystalline product. The H-1 NMR spectrum in deuterobenzene showed the following resonances:
Isolated racemic isomers:
singlets, 6H, 0.6δ
doublets, 4H, 5.85δ, 6.85δ
multiplets, 8H, 6.80δ, 7.1–7.4δ

Polymerization Examples

In the Examples following, the alumoxane employed was prepared by adding 45.5 grams of ferrous sulfate heptahydrate in four equally spaced increments over a two hour period to a rapidly stirred two liter round-bottom flask containing one liter of a 10.0 wt. percent solution of trimethylaluminum (TMA) in hexane. The flask was maintained at 50° C. under a nitrogen atmosphere. Methane produce was continuously vented. Upon completion of the addition of ferrous sulfate heptahydrate, the flask was continuously stirred and maintained at a temperature of 60° for six hours. The reaction mixture was cooled to room temperature and allowed to settle. The clear solution was separated from the solids by decantation.

Molecular weights were determined on a Water's Associates Model No. 150C GPC (Gel Permeation Chromatograph). The measurements were obtained by dissolving polymer samples in hot trichlorobenzene and filtering. The GPC runs are performed at 145° C. in trichlorobenzene at 1.0 ml/min flow using styragel columns from Perkin Elmer, Inc. 300 microliters of a 0.1% solution in trichlorobenzene were injected, and the samples were run in duplicate. The integration parameters were obtained with a Hewlett-Packard Data Module.

Example 12

A one liter stainless steel pressure vessel, equipped with an incline blade stirrer, an external jacket for temperature control, a septum inlet and vent line and a regulated supply of dry ethylene, propylene and nitrogen, was cleaned with boiling toluene and dried and deoxygenated with a nitrogen flow. The reactor temperature was adjusted to 20° C., and 200 cc of distilled, degassed toluene was added. Ten milliliters of a 0.8M toluene solution of methylalumoxane was injected, and the mixture was stirred at 0 psig under nitrogen. A toluene solution (10 cc) containing 5.00 mg of the racemic isomer of dimethylsilanylene bridged his tetrahydroindenyl zirconium dichloride, $(CH_3)_2Si(C_9H_{10})_2ZrCl_2$, was injected. Immediately 100 cc of liquid propylene was added, and the mixture was stirred for two hours at 20° C. The product was recovered by rapidly venting and opening the reactor. Residual toluene was evaporated in a stream of air, and the yield was weighed. The product was analyzed by gel permeation chromatography for molecular weight, by differential scanning calorimetry for melting point and by carbon-13 nuclear magnetic resonance spectrometry for tacticity. The results are given in Table 1.

Example 13

The polymerization of this example was performed as in Example 12 except that 5.00 mg of racemic dimethylsilanylene bridged bis (indenyl) zirconium dichloride, $(CH_3)_2Si(C_9H_6)_2ZrCl_2$, was substituted for the metallocene of Example 12. The results are tabulated in Table 1.

Example 14

The polymerization of this example was performed as in Example 12 except that 10.0 mg of racemic dimethylsilanylene bridged bis (methylcyclopentadienyl) zirconium dichloride, $(CH_3)_2Si(C_5H_3CH_3)_2ZrCl_2$, was substituted for the metallocene of Example 12. The results are tabulated in Table 1.

Example 15

The polymerization of this example was performed as in Example 12 except that 10.0 mg of racemic dimethylsilanylene bridged bis(trimethylsilanylcyclopentadienyl) zirconium dichloride, $(CH_3)_2Si(C_5H_3Si(CH_3)_3)_2ZrCl_2$, was substituted for the metallocene of Example 12. The results are tabulated in Table 1.

Example 16

The polymerization of this example was performed as in Example 12 except that 10.0 mg of tetramethyldisilanylene bridged bis(trimethylsilanylcyclopentadienyl) zirconium dichloride, $(CH_3)_4Si_2(C_5H_3Si(CH_3)_3)_2ZrCl_2$, was substituted for the metallocene of Example 12. The results are tabulated in Table 1.

Example 17

The polymerization of this example was performed as in Example 12 except that 10.0 mg of tetramethyldisilanylene bridged bis(methylcyclopentadienyl) zirconium dichloride, $(CH_3)_4Si_2(C_5H_3CH_3)_2ZrCl_2$, was substituted for the metallocene of Example 12. The results are tabulated in Table 1.

Example 18

The polymerization of this example was performed as in Example 12 except that 10.0 mg of racemic tetramethyldisiloxane bridged bis(tetrahydroindenyl) zirconium dichloride, $(CH_3)_4Si_2O(C_9H_{10})_2ZrCl_2$, was substituted for the metallocene of Example 12. The results are tabulated in Table 1.

Example 19

The polymerization of this example was performed as in Example 12 except that 10.0 mg of racemic tetramethyldisilanylene bridged bis(tetrahydroindenyl) zirconium dichloride, $(CH_3)_4Si_2(C_9H_{10})_2ZrCl_2$, was substituted for the metallocene of Example 12. The results are tabulated in Table 1.

Example 20

The polymerization of this example was performed as in Example 12 except that 10.0 mg of 2,2-dimethyl-2-silapropylene bridged bis(cyclopentadienyl) zirconium dichloride, $(CH_3)_2Si(CH_2)_2(C_5H_4)_2ZrCl_2$, was substituted for the metallocene of Example 12. The results are tabulated in Table 1.

Example 21

The polymerization of this example was performed as in Example 12 except that 10.0 mg of said metallocene was used and 100 cc of purified 4-methyl-1-pentene was substituted for the propylene of Example 12. The results are tabulated in Table 1.

Example 22

The polymerization of this example was performed as in Example 12 except that 100 cc of purified 1-octene was substituted for the propylene of Example 12. The results are tabulated in Table 1.

Example 23

The polymerization of this example was performed as in Example 12 except that 5.00 mg of racemic dimethylsilanylene bridged bis(indenyl) hafnium dichloride, $(CH_3)_2Si(C_9H_6)_2HfCl_2$, was substituted for the metallocene of Example 12. The results are tabulated in Table 1.

Example 24 - Comparative Example

The polymerization of this example was performed as in Example 12 except that 15.0 mg of racemic ethylene bridged bis(tetrahydroindenyl) zirconium dichloride rac-$(CH_2)_2(C_9H_{10})_2ZrCl_2$, was substituted for the metallocene of Example 12. The results are tabulated in Table 1.

Example 25 - Comparative Example

The polymerization of this example was performed as in Example 24 except that 10.0 mg of said metallocene was used and the polymerization was performed at 50° C. rather than 20° C. The results are tabulated in Table 1.

While an embodiment and application of this invention has been shown and described, it will be apparent to those skilled in the art that many more modifications are possible without departing from the inventive concepts herein described. The invention, therefore, is not to be restricted except as is necessary by the prior art and by the spirit of the appended claims.

TABLE I

| | | Polyrization Results | | | | |
|---|---|---|---|---|---|---|
| Example | Catalyst, mg | Cocatalyst, m moles | Yield, g | Mw | Melting point, °C. | Tacticity, % meso placements |
| 12 | rac-$(CH_3)_2Si(C_9H_{10})_2ZrCl_2$, 5.00 | methylalumoxane, 8.0 | 20.7 | 85,300 | 153.1 | 98.6 |
| 13 | rac-$(CH_3)_2Si(C_9H_6)_2ZrCl_2$, 5.00 | methylalumoxane, 8.0 | 11.8 | 73,000 | 149.0 | 97.6 |
| 14 | rac-$(CH_3)_2Si(C_5H_3CH_3)_2ZrCl_2$, 10.0 | methylalumoxane, 8.0 | 50.7 | 28,000 | 139.0 | 97.3 |
| 15 | rac-$(CH_3)_2Si(C_5H_3Si(CH_3)_3)_2ZrCl_2$, 10.0 | methylalumoxane, 8.0 | 48.0 | 63,000 | 142.0 | 97.5 |
| 16 | $(CH_3)_4Si_2(C_5H_3Si(CH_3)_3)_2ZrCl_2$, 10.0 | methylalumoxane, 8.0 | 26.5 | 31,500 | 108.1 | 88.2 |
| 17 | $(CH_3)_4Si_2(C_5H_3CH_3)_2ZrCl_2$, 10.0 | methylalumoxane, 8.0 | 26.1 | 20,600 | None | 63.9 |
| 18 | rac-$(CH_3)_4Si_2O(C_9H_{10})_2ZrCl_2$, 10.0 | methylalumoxane, 8.0 | 7.7 | 2,900 | None | 62.6 |
| 19 | rac-$(CH_3)_4Si_2(C_9H_{10})_2ZrCl_2$, 10.0 | methylalumoxane, 8.0 | 5.9 | 96,500 | 149.0 | 98.1 |

TABLE I-continued

| | | Polyrization Results | | | | |
|---|---|---|---|---|---|---|
| Example | Catalyst, mg | Cocatalyst, m moles | Yield, g | Mw | Melting point, °C. | Tacticity, % meso placements |
| 20 | $(CH_3)_2Si(CH_2)_2(C_5H_4)_2ZrCl_2$, 10.0 | methylalumoxane, 8.0 | 24.6 | 61,200 | None | 52.1 |
| 21 | rac-$(CH_3)_2Si(C_9H_{10})_2ZrCl_2$, 10.0 | methylalumoxane, 8.0 | 51.3 | 6,200 | 55.0 | n.d. |
| 22 | rac-$(CH_3)_2Si(C_9H_{10})_2ZrCl_2$, 5.0 | methylalumoxane, 8.0 | 39.1 | 5,900 | None | 92.0 |
| 23 | rac-$(CH_3)_2Si(C_9H_6)_2HfCl_2$, 5.0 | methylalumoxane, 8.0 | 8.2 | 550,000 | 149.3 | 98.2 |
| 24 | rac-$(CH_2)_2(C_9H_{10})_2ZrCl_2$, 15.0 | methylalumoxane, 8.0 | 53.0 | 30,400 | 141.0 | 97.3 |
| 25 | rac-$(CH_2)_2(C_9H_{10})_2ZrCl_2$, 10.0 | methylalumoxane, 8.0 | 32.5 | 5,200 | 128.7 | 94.2 |

What is claimed is:

1. A method for producing a compound represented by the formula:

wherein M' is a Group IVB transition metal;

X' and X" are the same or different hydride, halogen, or hydrocarbyl or halohydrocarbyl having up to about 6 carbon atoms;

A' and A" are the same or different asymmetrical mononuclear or polynuclear hydrocarbyl or silahydrocarbyl moieties; and S' is a bridge of 1–4 atoms selected from the group consisting of silanylene, silaalkylene, oxasilanylene, and oxasilaalkylene, a) combining:
  i) a bridged bis-(substituted cyclopentadienide) dialkali metal compound; and
  ii) a transition metal halide, and
b) recovering the represented stereorigid chiral compound.

2. A process for the preparation of a chiral, stereorigid metallocene compound of the formula I

[R¹R²Si(indenyl)₂]Y²X₂ in which R¹ and R² are identical or different and denote a selection from the group consisting of silanylene, silaalkylene, oxasilanylene, and ocasilaalkylene, Y² is titanium, zirconium or hafnium, and X denotes a halogen atom, which comprises reacting a compound of formula II

[R¹R²Si(indenyl)₂]Y₂¹ in which R¹ and R² have the above mentioned meaning and Y¹ is an alkali metal, with a compound of the formula III

Y²X₄ in which Y² and X have the above mentioned meaning, at a temperature of from −78° C. to 25° C. in an inert solvent for a reaction time ranging from 10 to 1000 minutes, and recovering said compound of formula I from the inert solvent.

3. A catalyst system for the polymerization of olefins, comprising, as a component, a transition metal compound represented by the formula:

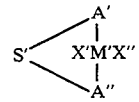

wherein M' is a transition metal;

X' and X" are the same of different hydride, halogen, hydrocarbyl or halohydrocarbyl having up to about 6 carbon atoms;

A' and A" are each the same or different asymmetrical mononuclear or polynuclear hydrocarbyl or silahydrocarbyl moieties; and S' is a bridge of 1–4 atoms selected from the group consisting of silanylene, silaalkylene, oxasilanylene and oxasilaalkylene.

4. A catalyst system, at least one component of which is on a support, for the polymerization of olefins, comprising, as a component, a transition metal compound represented by the formula:

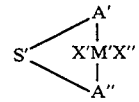

wherein M' is a transition metal;

X' and X" are the same or different hydride, halogen, hydrocarbyl or halohydrocarbyl having up to about 6 carbon atoms;

A' and A" are each the same or different asymmetrical mononuclear or polynuclear hydrocarbyl or silahydrocarbyl moieties; and S' is a bridge of 1–4 atoms selected from the group consisting of silanylene, silaalkylene, oxasilanylene and oxasilaalkylene.

5. A catalyst system for the polymerization of olefins, comprising:

(a) A transition metal compound represented by the formula:

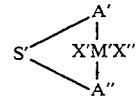

wherein M' is a transition metal;

X' and X" are the same or different hydride, halogen, hydrocarbyl or halohydrocarbyl having up to about 6 carbon atoms;

A' and A" are each the same or different asymmetrical mononuclear or polynuclear hydrocarbyl or silahydrocarbyl moieties; and S' is a bridge of 1-4 atoms selected from the group consisting of silanylene, silaalkylene, oxasilanylene and oxasilaalkylene; and (b) alumoxane.

6. The catalyst system of claim 5, wherein M' is titanium, zirconium, or hafnium.

7. The catalyst system of claim 5, wherein X' and X" are independently chlorine, bromine, or iodine.

8. The catalyst system of claim 5, wherein X' and X" are independently alkyl or haloalkyl of 1-6 carbon atoms.

9. The catalyst system of claim 5, wherein A' and A" are represented by the formula:

wherein n is an integer of from 1 to 4 and each R' is the same or different hydrocarbyl or silahydrocarbyl of 1-20 carbon atoms or taken together, two or more of R' are hydrocarbylene or silahydrocarbylene of 1-20 carbon atoms.

10. The catalyst system of claim 5, wherein each silicon atom is disubstituted with the same or different lower hydrocarbyl.

11. The catalyst system of claim 5 in racemic mixture.

12. A catalyst system for the polymerization of olefins; comprising:

A. A chiral transition metal compound substantially free of achiral forms thereof, said compound having the formula:

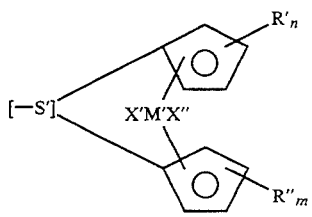

wherein M' is titanium, zirconium or hafnium;
X' and X" are the same or different hydride, chlorine, bromine, iodine, or 1-6 carbon-atom alkyl, haloalkyl, aryl, or haloaryl;
n and m are the same or different integers from 1 to 4;
R' and R" are the same or different hydrocarbyl or silahydrocarbyl of 1-20 carbon atoms, and 0-2 silicon atoms, or taken together, two or more of R' or of R" are hydrocarbylene or silahydrocarbylene of 1-20 carbon atoms and 0-2 silicon atoms; and
S' is a chain of 0-4 carbon atoms and 1-2 silicon atoms selected from the group consisting of silanylene, silaalkylene, oxasilanylene and oxasilaalkylene, in which each silicon atom is disubstituted with the same or different lower hydrocarbyl, and
B. alumoxane.

13. The catalyst system of claim 12, wherein M' is titanium.

14. The catalyst system of claim 12, wherein X' and X" are chlorine.

15. The catalyst system of claim 12, wherein R' and R" are butylene, butadienylene, methyl, isobutyl or trimethylsilanyl.

16. The catalyst system of claim 12, wherein S' is dialkylsilanylene, 1-sila-1,1-dialkyl ethylene, tetraalkyldisilanylene, 2-sila-2,2-dialkyl propylene, 1,3-disila-1,1,3,3-tetraalkyl propylene, dialkylsiloxy (dialkyl) silanylene or 1,4-disila-1,1,4,4-tetraalkyl butylene.

17. The catalyst system of claim 12, wherein the transition metal compound is racemic [1,1'-dimethylsilanylene-bis(3methylcyclopentadienyl)] zirconium dichloride.

18. The catalyst system of claim 12, wherein the transition metal compound is racemic [1,1'-dimethylsilanylene-bis(indenyl)] zirconium dichloride.

19. The catalyst system of claim 12, wherein the transition metal compound is racemic [1,1'-dimethylsilanylene-bis(4,5,6, 7-tetrahydroindenyl)] zirconium dichloride.

20. The catalyst system of claim 12, wherein the transition metal compound is racemic [1,1'-(1,1,2,2-tetramethyldisilanylene)-bis(3-methylcyclopentadienyl)] zirconium dichloride.

21. The catalyst system of claim 12, wherein the transition metal compound is racemic [1,1'-(1,1,2,2-tetramethyldisilanylene)-bis(4,5,6,7-tetrahydroindenyl)] zirconium dichloride.

22. The catalyst system of claim 12, wherein the transition metal compound is racemic [1,1'-(dimethylsilanylene-bis(3-trimethylsilanylcyclopentadienyl)] zirconium dichloride.

23. The catalyst system of claim 12, wherein the transition metal compound is racemic [1,1'-(1,1,2,2-tetramethyldisilanylene)-bis(3-trimethylsilanylcyclopentadienyl)] zirconium dichloride.

24. The catalyst system of claim 12, wherein the transition metal compound is racemic [1,1'-(1,1,3,3-tetramethyldisilanylene)-bis(4,5,6,7-tetrahydroindenyl)] zirconium dichloride.

25. The catalyst system of claim 12, wherein the transition metal compound is racemic [1,1'-(1,1,2,2-tetramethyldisilanylene)-bis(4,5,6,7-tetrahydroindenyl)] zirconium dichloride.

26. The catalyst system of claim 12, wherein the transition metal compound is racemic [1,1'-(1,1,2,2-dimethyl-2-silapropylene)-bis(3-methylcyclopentadienyl)] zirconium dichloride.

27. The catalyst system of claim 12, wherein the transition metal compound is racemic [1,1'-(1,1,2,2-dimethylsilanylene-bis(3-methylcyclopentadienyl)] hafnium dichloride.

28. The catalyst system of claim 12, wherein the transition metal compound is racemic [1,1'-Odimethylsilanylene-bis(indenyl)] hafnium dichloride.

29. The catalyst system of claim 12, wherein the transition metal compound is racemic [1,1'-dimethylsilanylene-bis(4,5,6,7-tetrahydroindenyl)] hafnium dichloride.

30. The catalyst system of claim 12, wherein the transition metal compound is racemic [1,1'-(1,1,2,2-tetramethyldisilanylene)-bis(3-methylcyclopentadienyl)] hafnium dichloride.

31. The catalyst system of claim 12, wherein the transition metal compound is racemic [1,1'-(1,1,2,2-tetramethyldisilanylene)-bis(4,5,6,7-tetrahydroindenyl)] hafnium dichloride.

32. The catalyst system of claim 12, wherein the transition metal compound is racemic [1,1'-dimethylsilanylene-bis(3-trimethylsilanylcyclopentadienyl)] hafnium dichloride.

33. The catalyst system of claim 12, wherein the transition metal compound is racemic [1,1'-(1,1,2,2-tetramethyldisilanylene)-bis(3-trimethylsilanylcyclopentadienyl)] hafnium dichloride.

34. The catalyst system of claim 12, wherein the transition metal compound is racemic [1,1'-(1,1,2,2-tetramethyldisilanylene)-bis(4,5,6,7-tetrahydroindenyl)] hafnium dichloride.

35. The catalyst system of claim 12, wherein the transition metal compound is racemic [1,1'-(1,1,2.2-dimethyl-2-silapropylene)-bis(3-methylcyclopentadienyl)] hafnium dichloride.

36. The catalyst system in accordance with claim 5 which further comprises an inorganic oxide porous support.

37. The catalyst system in accordance with claim 12 which further comprises an inorganic oxide porous support.

* * * * *